(12) United States Patent
Baroni et al.

(10) Patent No.: US 8,202,871 B2
(45) Date of Patent: Jun. 19, 2012

(54) INDOL-2-ONE DERIVATIVES DISUBSTITUTED IN THE 3-POSITION, PREPARATION THEREOF AND THERAPEUTIC USE THEREOF

(75) Inventors: Marco Baroni, Milan (IT); Letizia Puleo, Milan (IT)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 13/012,321

(22) Filed: Jan. 24, 2011

(65) Prior Publication Data

US 2011/0118280 A1    May 19, 2011

Related U.S. Application Data

(63) Continuation of application No. 12/702,687, filed on Feb. 9, 2010, now abandoned, which is a continuation of application No. PCT/FR2008/001190, filed on Aug. 14, 2008.

(30) Foreign Application Priority Data

Aug. 16, 2007 (FR) ...................................... 07 05858

(51) Int. Cl.
| | |
|---|---|
| A61K 31/496 | (2006.01) |
| A61K 31/454 | (2006.01) |
| A61K 31/4439 | (2006.01) |
| C07D 209/40 | (2006.01) |
| C07D 401/12 | (2006.01) |
| C07D 401/14 | (2006.01) |
| C07D 405/04 | (2006.01) |
| C07D 409/12 | (2006.01) |
| C07D 409/14 | (2006.01) |
| C07D 417/04 | (2006.01) |
| C07D 417/141 | (2006.01) |

(52) U.S. Cl. ......... 514/253.09; 514/254.02; 514/254.09; 514/318; 514/323; 514/339; 544/364; 544/368; 544/373; 546/194; 546/201; 546/277.7; 548/483; 548/159

(58) Field of Classification Search .................. None
See application file for complete search history.

(56) References Cited

U.S. PATENT DOCUMENTS 5,594,023 A * 1/1997 Wagnon et al. ................ 514/423

FOREIGN PATENT DOCUMENTS

| WO | WO 95/18105 | 7/1995 |
| WO | WO 00/10975 | 3/2000 |
| WO | WO 03/008407 | 1/2003 |
| WO | WO 2005/035498 | 4/2005 |

OTHER PUBLICATIONS

Carpino et al. Expert Opin. Ther.Patents 18(11), p. 1253-1263 (2008).*

Brazzoni, R., et al., Ghrelin Regulates Mitochondrial-Lipid Metabolism Gene Expression and Tissue Fat Distribution in Liver Skeletal Muscle, Am J. Physiol Endocrinol Metab., vol. 288, pp. E228-E235, (2005).

Dass, N.B., et al., Growth Hormone Secretagogue Receptors in Rat and Human Gastrointestinal Tract and the Effects of Ghrelin, Neuroscience, vol. 120, (2003), pp. 443-453.

Depoortere, I., et al., Comparison of the Gastroprokinetic Effects of Ghrelin, GHRP-8 and Motilin in Rats in Vivo and in Vitro, European Journal of Pharmacology, vol. 515, (2005), pp. 160-168.

Dezaki, K., et al., Endogenous Ghrelin in Pancreatic Islets Restricts Insulin Research by Attenuating Ca2+ Signaling in B-Cells Implication in the Glycemic Control in Rodents, Diabetes, vol. 53, pp. 3142-3151, (2004).

Druce, M.R., et al., Ghrelin Increases Food Intake in Obese As Well As Lean Subjects, International Journal of Obesity, vol. 29, pp. 1130-1136, (2005).

Fukuda, H., et al., Ghrelin Enhances Gastric Motility Through Direct Stimulation of Intrinsic Neural Pathways and Capsaicin-Sensitive Afferent Neurones in Rats, Scand. J. Gastroenterol, vol. 12, pp. 1209-1214, (2004).

Kojima, M., et al., Ghrelin is a Growth-Hormone-Releasing Acylated Peptide From Stomach, Nature, (1999), vol. 402, pp. 656-660.

Prado, C.L., et al., Ghrelin Celis Replace Insulin-Producing B. Cells in two Mouse Models of Pancreas Development, Proc. Natl., Acad. Sci., vol. 101, pp. 2924-2929, (2004).

Sun., Y, et al., Ablation of Ghrelin Improves the Diabetic But Not Obese Phenotype of ob/ob Mice, Cell Metabolism, vol. 3, pp. 379-386, (2006).

(Continued)

*Primary Examiner* — Emily Bernhardt
(74) *Attorney, Agent, or Firm* — Scully, Scott, Murphy & Presser, P.C.

(57) ABSTRACT

The present application discloses compounds of the formula:

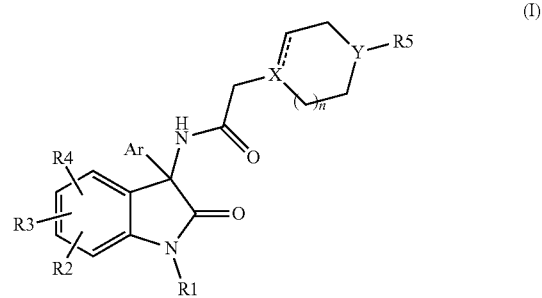

and pharmaceutical compositions containing same and their use for treating and preventing various pathologies, including obesity, appetite disorders, excess weight and diabetes.

19 Claims, No Drawings

OTHER PUBLICATIONS

Ueno, N., et al., Leptin Modulates Orexigenic Effects of Gherline and Attenuates Adiponectin and Insulin Levels and Selectivity the Dark-Phase Feeding as Revealed by Central Leptin Gene Therapy, Endocrinology, vol. 145, No. 9, pp. 4176-4184 (2004).

Wren, A.M., et al., Gherlin Enhances Appetite and Increases Food Intake in Humans, The Journal of Endicrinology & Metabolism, vol. 86, No. 12, pp. 5992-5995. (2001).

Wynne, K., et al., Subcutaneous Ghrelin Enhances Acute Food Intake in Mal-nourished Patients Who Receive Maintenance Peritoneal Dialysis; A Randomized, Placebo-Controlled Trial, J. Am. Soc. Nephrol. vol. 16, pp. 2111-2118 (2005).

Ratkowsky, D.A., et al., Choosing Near-Linear Parameters in the Four-Parameter Logistic Model for Radioiigand and Related Assays, Biometrics, vol. 42, pp. 575-582, (1986).

Bunce, R.A., et al., Dibenzo-Fused Seven-Membered Nitrogen Heterocyles by a Tandem Reduction-Lactamization Reaction, J. Heterocyclic Chem., vol. 43, (2006), pp. 1031-1035.

* cited by examiner

INDOL-2-ONE DERIVATIVES DISUBSTITUTED IN THE 3-POSITION, PREPARATION THEREOF AND THERAPEUTIC USE THEREOF

CROSS REFERENCE TO RELATED APPLICATIONS

This application is a continuation of U.S. Ser. No. 12/702,687, filed Feb. 9, 2010.

The present invention relates to 3-disubstituted indol-2-one derivatives, to their preparation and to their therapeutic application.

Ghrelin is a 28 amino-acid peptide hormone produced mainly in the stomach by a post-translational process after cleavage of pre-pro-ghrelin (Kojima M., et al., *Nature* 1999; 402: 656-60). Ghrelin is an endogenous ligand of the growth hormone secretagogue pituitary receptor (GHSR1a).

GHS-R is encoded by two exons: exon 1 encodes the transmembrane domains (TMs) 1-5 and exon 2 encodes TM6 and 7 of the G-protein-coupled receptor (GPCR).

The two transcripts have been identified in the pituitary gland and the brain: one encoding the full-length GPCR (GHS-R1a) and the other encoding a truncated receptor (GHS-R1b) lacking TM6 and 7. Only the subtype GHS-R1a is activated by ghrelin and ghrelin mimetics. GHS-R1b is present in the liver and other peripheral tissues, but its function is unknown (Smith R. G. et al., *Trends in Endocrinology and Metabolism*, 2005, 16, No. 9).

It is a receptor of rhodopsin type, with seven transmembrane domains of family A coupled to Gq/phospholipase C. The ghrelin receptor may also be coupled to the Gs/protein kinase A pathways in certain tissues (Ueno, N. et al., *Endocrinology*, 2004, 145, 4176-4184; Kim, M. S. et al., *Int. J. Obes. Relat. Metab. Disord.*, 2004, 28: 1264-1271). Interestingly, the ghrelin receptor has the relatively uncommon characteristic of having significant ligand-independent constitutive activity (Barazzoni, R. et al., *Am. J. Physiol. Endocrinol. Metab.*, 2004, 288: E228-E235).

Low levels of expression of ghrelin have been documented in various tissues, such as the intestines, the pancreas, the kidneys, the immune system, the placenta, the testicles, pituitary tissue and the hypothalamus (*Horm. Res.* 2003; 59 (3): 109-17).

It has been demonstrated that ghrelin is involved in hunger at mealtimes, and in the initiation of meals. The circulating levels decreases with the intake of food and increase after meals, reaching concentrations that are sufficient to stimulate hunger and the intake of food. Ingestion of ghrelin stimulates food intake rapidly and transiently, mainly by increasing the appetitive feeding behaviour and the number of meals. Ghrelin stimulates the short-term taking of food more efficiently than any other molecule, with the exception of neuropeptide Y, with which it is approximately equipotent (Wren A. M. et al., *J. Clin. Endocrinol. Metab.*, 2001; 86: 5992-5). However, ghrelin is unique in its capacity to exert this effect, whether it is injected peripherally or centrally.

It is also the only mammalian substance that has demonstrated its capacity to increase the appetite and the taking of food when it is administered to humans (Druce M. R., et al., *Int. J. Obes.*, 2005; 29: 1130-6; Wynne K., et al., *J. Am. Soc. Nephrol.*, 2005; 16: 2111-8).

Beyond its role in the initiation of meals, ghrelin also satisfies the established criteria of an adiposity-related hormone involved in regulating the long-term body mass. The levels of ghrelin circulate as a function of the energy reserves and display compensatory changes in response to changes in body mass.

Ghrelin crosses the blood-brain barrier and stimulates the taking of food by acting on certain standard body mass-regulating centres, such as the hypothalamus, the hindbrain and the mesolimbic compensatory system.

Chronic administration of ghrelin increases the body mass via diverse concerted actions on the taking of food, energy expenditure and the utilisation of resources. Congenital ablation of ghrelin or of the ghrelin receptor gene causes a resistance to feeding-induced obesity, and pharmacological blocking of ghrelin reduces the intake of food and the body mass.

The existing evidence appears to favour the role of ghrelin both in the short-term initiation of meals and long-term energy homeostasis, thus making it an attractive target as a medicament for treating obesity and/or slimming disorders.

Ghrelin also exerts both physiological and pharmacological actions on the endocrine pancreas. Acylated bioactive ghrelin is produced in the ε cells, recently described in the pancreatic islets (Prado, C. L., et al., 2004, *Proc. Natl. Acad. Sci. USA*, 101: 2924-2929), potentially providing a local source of ghrelin that acts on the β cells of the islets. Blockage of this function of endogenous ghrelin by means of an antagonist for its receptors substantially reduced the fasted glucose concentrations, attenuated the glycaemic movement and increased the responses to insulin during glucose tolerance tests, suggesting an inhibitory role of ghrelin in the control of insulin secretion (Dezaki, K., et al. 2004, *Diabetes*, 53: 3142-3151).

Ablation of ghrelin in mice (ghrelin −/− mice) increases the glucose-dependent secretion of insulin by the β cells of the pancreas, by reducing the Ucp2 expression and increases the sensitivity to peripheral insulin (Sun Y. et al., 2006, *Cell Metabolism*, 3: 379-386).

Ghrelin receptor antagonists could thus regulate hunger, the taking of meals and their frequency, and also, in the long-term, the weight, especially weight gain following diets or therapeutic regimens. Furthermore, in the context of an antidiabetic treatment, ghrelin antagonists could be useful for maintaining the equilibrium between insulin and glucose for controlling diabetic hyperphagia. Ghrelin antagonists could thus be used as anorexic and/or anti-obesity agents, or alternatively in the treatment of diabetes and its effects.

Patent application WO 95/18105 describes 5-chloro-3-(2-chlorophenyl)-1,3-dihydro-3-[2-(4-methylpiperazin-1-yl) acetamido]indol-2-one and 5-chloro-3-(2-chloroacetamido)-3-(2-chlorophenyl)-1,3-dihydroindol-2-one compounds as synthetic intermediates for 1,3-dihydroindol-2-one derivatives 3-substituted with a nitrogenous group and having affinity for vasopressin and/or oxytocin.

One subject of the present invention is compounds corresponding to formula (I):

$$\text{(I)}$$

in which:
----- represents a single or double bond,
X represents —N<, —CH< or $$-\overset{\displaystyle\parallel}{\underset{\displaystyle\diagdown}{C}}\ ;$$

Y represents >N— or >CH—, it being understood that at least one from among X and Y represents N;
Ar represents an aryl or heteroaryl group optionally substituted with one or more substituents, which may be identical or different, chosen from halogen atoms and (C1-6)alkyl, (C1-6)haloalkyl, perhalo(C1-3)alkyl, (C1-6)alkoxy, perhalo(C1-3)alkoxy and aryl groups;
R1 represents a hydrogen atom or a (C1-6)alkyl, —C(=O)(C1-6)alkyl or —C(=O)aryl group;
R2, R3 and R4, which may be identical or different, located on any of the available positions of the phenyl nucleus, independently represent a hydrogen atom, a halogen atom, CN, OH, a (C1-6)alkyl group optionally substituted with a halogen atom or an OH; perhalo(C1-3)alkyl, (C1-6)alkoxy, perhalo(C1-3)alkoxy, aminocarbonyl, (C1-6)alkylaminocarbonyl, di(C1-6)alkylamino-carbonyl, aryl, aryloxy; heteroaryl; the aryl, aryloxy or heteroaryl group possibly being optionally substituted with a halogen atom, CN, OH or a (C1-6)alkyl, perhalo(C1-3)alkyl or (C1-6)alkoxy group; it being understood that at least one from among R2, R3 and R4 is other than H and that the aryl, aryloxy or heteroaryl group may be optionally substituted with a halogen atom, CN, OH or a (C1-6)alkyl, perhalo(C1-3)alkyl or (C1-6)alkoxy group;
R5 represents a (C1-6)alkyl or (C2-6)alkenyl group; and
n represents 1 or 2; with the exclusion of 5-chloro-3-(2-chlorophenyl)-1,3-dihydro-3-[2-(4-methylpiperazin-1-yl)acetamido]indol-2-one.

The compounds of formula (I) comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or of acid-addition salts. Such addition salts form part of the invention.

These salts may be prepared with pharmaceutically acceptable acids, but the salts of other acids that are useful, for example, for purifying or isolating the compounds of formula (I) also form part of the invention.

In the context of the present invention, the following definitions apply:
a halogen atom: a fluorine, a chlorine, a bromine or an iodine;
an alkyl group: a linear or branched saturated aliphatic group. Examples that may be mentioned include a (C1-6)alkyl group containing from 1 to 6 carbon atoms, more particularly (C1-4)alkyl, which may represent a methyl, ethyl, propyl, isopropyl, butyl, isobutyl or tert-butyl;
an alkenyl group: a linear or branched, monounsaturated or polyunsaturated aliphatic group comprising, for example, one or two unsaturations and containing from 2 to 6 carbon atoms;
a haloalkyl group: an alkyl group in which one or more hydrogen atoms have been replaced with a halogen atom; for example a fluoroalkyl: an alkyl group in which one or more hydrogen atoms have been replaced with a fluorine atom;
a perhaloalkyl group: an alkyl group in which all the hydrogen atoms have been replaced with a halogen atom; for example, a perfluoroalkyl: an alkyl group in which all the hydrogen atoms have been replaced with a fluorine atom;
an alkoxy group: a radical —O-alkyl in which the alkyl group is as defined above;
a perhaloalkoxy group: a radical —O-perhaloalkyl in which the perhaloalkyl group is as defined above; mention may be made, for example, of trifluoromethoxy;
an aryl group: a cyclic aromatic group containing between 6 and 10 carbon atoms. Examples of aryl groups that may be mentioned include phenyl and naphthyl;
a heteroaryl group: a cyclic aromatic group containing between 2 and 10 carbon atoms and comprising between 1 and 3 heteroatoms, such as nitrogen, oxygen or sulfur. Examples of heteroaryl groups that may be mentioned include furyl, pyrrolyl, imidazolyl, pyrazolyl, thienyl, oxadiazolyl, oxazolyl, isoxazolyl, furazanyl, thiadiazolyl, thiazolyl, isothiazolyl, pyridyl, pyrazinyl, pyrimidinyl and pyridazinyl groups, and also the corresponding groups resulting from fusion with a phenyl group, for instance benzothiophene, benzofuran, benzothiazole, etc.

Among the compounds of formula (I) that are subjects of the invention, one group of compounds is constituted by the compounds for which:
Ar represents an aryl or heteroaryl group optionally substituted with one or more substituents, which may be identical or different, chosen from halogen atoms and (C1-6)alkyl, perhalo(C1-3)alkyl, (C1-6)alkoxy and aryl groups;
R1 represents a hydrogen atom or a (C1-6)alkyl, —C(=O)(C1-6)alkyl or —C(=O)aryl group;
R2, R3 and R4, which may be identical or different, located on any of the available positions of the phenyl nucleus, independently represent a hydrogen atom, a halogen atom, CN, OH or a (C1-6)alkyl, perhalo(C1-3)alkyl, (C1-6)alkoxy, perhalo(C1-3)alkoxy, aminocarbonyl, (C1-6)alkylaminocarbonyl, di(C1-6)alkylaminocarbonyl, aryl, aryloxy or heteroaryl group, it being understood that at least one from among R2, R3 and R4 is other than H;
R5 represents a (C1-6)alkyl group.

Among the compounds of formula (I) that are subjects of the invention, one group of compounds is constituted by the compounds for which:

----- represents a single or double bond; and/or

X represents —N<, —CH< or

and/or

Y represents >N— or >CH—, and/or it being understood that at least one from among X and Y represents N;

and/or

Ar represents an aryl group optionally substituted with one or more substituents chosen from halogen atoms, preferentially chlorine or bromine, and (C1-6)alkoxy, (C1-6)alkyl, aryl, trifluoromethyl and trifluoromethoxy groups; and/or R1 represents a hydrogen atom or a —C(=O)(C1-6)alkyl, —C(=O)aryl or (C1-6)alkyl group; and/or R2, R3 and R4, which may be identical or different, located on any of the available positions of the phenyl nucleus, independently represent a hydrogen atom, a halogen atom, preferentially chlorine or bromine, or a (C1-6)alkyl or trifluoromethyl group, it being understood that at least one from among R2, R3 and R4 is other than H; and/or R5 represents a (C1-6)alkyl group; and/or n represents 1 or 2;

in the form of the base or of an acid-addition salt.

Among the compounds of formula (I) that are subjects of the invention, another group of compounds is constituted by the compounds for which:

----- represents a single or double bond; and/or

X represents —N<, —CH< or

and/or

Y represents >N— or >CH—, and/or it being understood that at least one from among X and Y represents N; and/or Ar represents a phenyl or naphthyl group optionally substituted with one or more substituents chosen from halogen atoms, preferentially chlorine or bromine, and methoxy, methyl, tert-butyl, phenyl, trifluoromethyl and trifluoromethoxy groups; and/or R1 represents a hydrogen atom or a —C(=O)methyl, —C(=O)phenyl or methyl group; and/or R2, R3 and R4, which may be identical or different, located on any of the available positions of the phenyl nucleus, independently represent a hydrogen atom, a halogen atom, preferentially chlorine or bromine, or a methyl or trifluoromethyl group, it being understood that at least one from among R2, R3 and R4 is other than H; and/or R5 represents a methyl, ethyl or 2-propyl group; and/or n represents 1 or 2;

in the form of the base or of an acid-addition salt.

Among the compounds of formula (I) that are subjects of the invention, another group of compounds is constituted by the compounds for which:

Ar represents a heteroaryl group optionally substituted with one or more substituents, which may be identical or different, chosen from halogen atoms and (C1-6)alkyl, perhalo(C1-3) alkyl, (C1-6)alkoxy and aryl groups.

Among the compounds of formula (I) that are subjects of the invention, mention may be made especially of the following compounds:

(+)-N-[5,6-dichloro-3-(4-chlorophenyl)-2-oxo-2,3-dihydro-1H-indol-3-yl]-2-(4-methylpiperazin-1-yl)acetamide (+)-N-[4,6-dichloro-3-(4-trifluoromethylphenyl)-2-oxo-2,3-dihydro-1H-indol-3-yl]-2-(1-ethylpiperid-4-yl)acetamide N-[4,6-dichloro-3-(4-chlorophenyl)-2-oxo-2,3-dihydro-1H-indol-3-yl]-2-(4-methylpiperazin-1-yl)acetamide N-[4-trifluoromethyl-6-cyano-3-(4-chlorophenyl)-2-oxo-2,3-dihydro-1H-indol-3-yl]-2-(4-ethylpiperazin-1-yl)acetamide (+)-N-[1-benzoyl-5,6-dichloro-3-(4-chlorophenyl)-2-oxo-2,3-dihydro-1H-indol-3-yl]-2-(4-methylpiperazin-1-yl)acetamide 3-(4-chlorophenyl)-3-[2-(4-ethylpiperazin-1-yl)acetylamino]-2-oxo-4-trifluoromethyl-2,3-dihydro-1H-indole-6-carboxamide N-[6-chloro-3-(4-chlorophenyl)-1,5-dimethyl-2-oxo-2,3-dihydro-1H-indol-3-yl]-2-(4-methylpiperazin-1-yl)acetamide (+)-N-[4,6-dichloro-3-(4-trifluoromethylphenyl)-2-oxo-2,3-dihydro-1H-indol-3-yl]-2-(1-ethyl-1,2,3,6-tetrahydropyrid-4-yl)acetamide N-[4,6-dichloro-3-(3,4-dichlorophenyl)-2-oxo-2,3-dihydro-1H-indol-3-yl]-2-(4-ethylpiperazin-1-yl)acetamide N-[4,6-dichloro-3-(3-fluoro-4-chlorophenyl)-2-oxo-2,3-dihydro-1H-indol-3-yl]-2-(4-ethylpiperazin-1-yl)acetamide N-[4,6-dichloro-3-(3-trifluoromethyl-4-chlorophenyl)-2-oxo-2,3-dihydro-1H-indol-3-yl]-2-(4-ethylpiperazin-1-yl)acetamide N-[4,6-dichloro-1-ethyl-3-(2-methylbenzo[b]thiophen-5-yl)-2-oxo-2,3-dihydro-1H-indol-3-yl]-2-(1-ethylpiperid-4-yl)acetamide N-[4,6-dichloro-1-ethyl-3-(2-methyl-5-benzofuryl)-2-oxo-2,3-dihydro-1H-indol-3-yl]-2-(4-ethylpiperazin-1-yl)acetamide N-[4,6-dichloro-3-(4-trifluoromethoxyphenyl)-2-oxo-2,3-dihydro-1H-indol-3-yl]-2-(4-ethylpiperazin-1-yl)acetamide in the form of the base or of an acid-addition salt.

In the text hereinbelow, the term "protecting group Pg" means a group that makes it possible firstly to protect a reactive function such as a hydroxyl or an amine during a synthesis, and, secondly, to regenerate the intact reactive function at the end of the synthesis. Examples of protecting groups and of protection and deprotection methods are given in *Protective Groups in Organic Synthesis*, Greene et al., 2nd edition (John Wiley & Sons, Inc., New York).

In the text hereinbelow, the term "leaving group" means a group that may be readily cleaved from a molecule by breaking a heterolytic bond, with loss of an electron pair. This group may thus be readily replaced with another group during a substitution reaction, for example. Such leaving groups are, for example, halogens or an activated hydroxyl group such as a methanesulfonate, benzenesulfonate, p-toluenesulfonate, triflate, acetate, etc. group. Examples of leaving groups and references for their preparation are given in *Advances in Organic Chemistry*, J. March, 3rd edition, Wiley Interscience, pp. 310-316.

In accordance with the invention, the compounds of general formula (I) may be prepared according to the process that follows:

Scheme 1:

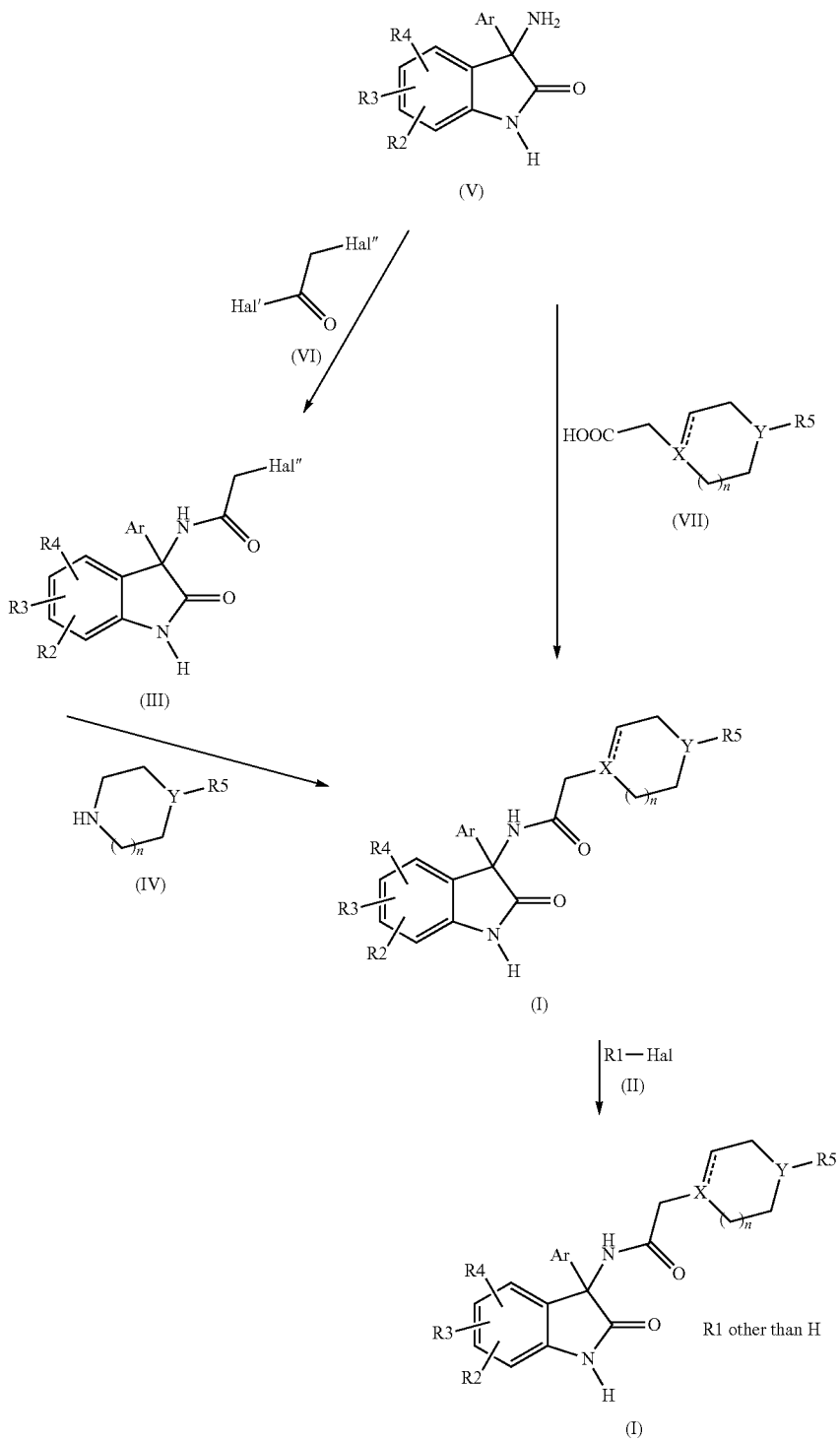

The compound of formula (I), in which R1 is other than H and , R2, R3, R4, R5, Ar, X, Y and n are as defined in the general formula (I), may be prepared by reacting a compound of formula (I) in which R1=H with a compound of formula (II):

R1-Hal  (II)

in which R1, which is other than H, is defined as in the general formula (I) and Hal represents a halogen atom, for example chlorine, according to methods known to those skilled in the art, for example in the presence of a base such as $K_2CO_3$, NaH or t-BuO⁻K⁺, in a solvent such as dimethylformamide (DMF), tetrahydrofuran (THF), dimethoxyethane or dimethyl sulfoxide (DMSO).

The compound of general formula (I) in which R1=H may be prepared according to one or other of the following variants:

When X=—N<, the compound of general formula (I) in which R1=H, i.e. the compound of general formula (II), may be prepared by reacting a compound of general formula (III):

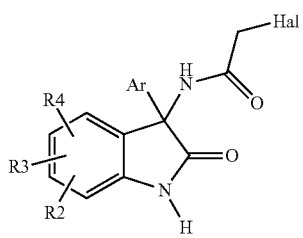

(III)

with a compound of general formula (IV):

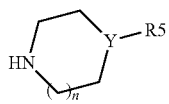

(IV)

in which Y, R2, R3, R4, R5, Ar and n are as defined in the general formula (I). This reaction is generally performed using an organic or mineral base, such as $K_2CO_3$, $Na_2CO_3$, pyridine or 4-dimethylaminopyridine, in the presence of NaI or KI, in an inert solvent such as DMF, dichloromethane, THF, dimethoxyethane or toluene.

The compound of general formula (III) may be prepared from a compound of general formula (V):

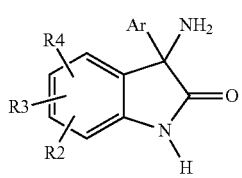

(V)

and from a compound of general formula (VI):

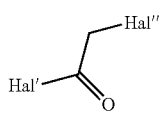

(VI)

in which R2, R3, R4, R5 and Ar are as defined in the general formula (I) and Hal' and Hal", which may be identical or different, independently represent a halogen atom, preferably chlorine.

This reaction is generally performed using pyridine or 4-dimethylaminopyridine in a solvent such as toluene, benzene or dichloromethane, preferentially at a temperature of between room temperature and the reflux point of the solvent.

When X=—CH, —N< or

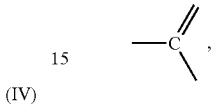

the compound of general formula (I) in which R1=H may also be prepared from a compound of general formula (V):

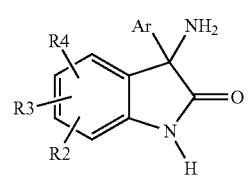

(V)

and from a compound of general formula (VII):

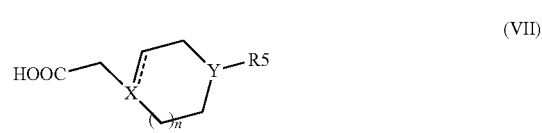

(VII)

in which ----, R2, R3, R4, R5, Ar, X, Y and n are as defined in the general formula (I). This reaction is generally performed using a halogenating agent, such as a chlorinating agent, for example phosphorus chlorides, especially $PCl_5$, or alternatively $PCl_3$ or $POCl_3$. The reaction is generally performed in the presence of pyridine or 4-dimethylaminopyridine, in a solvent such as dichloromethane or DMF.

The intermediates of general formula (V) are known and may be prepared according to the processes illustrated by scheme that follows:

Scheme 2:

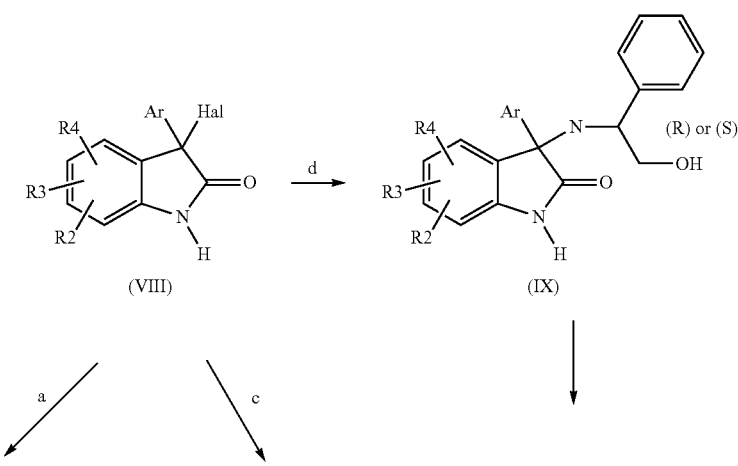

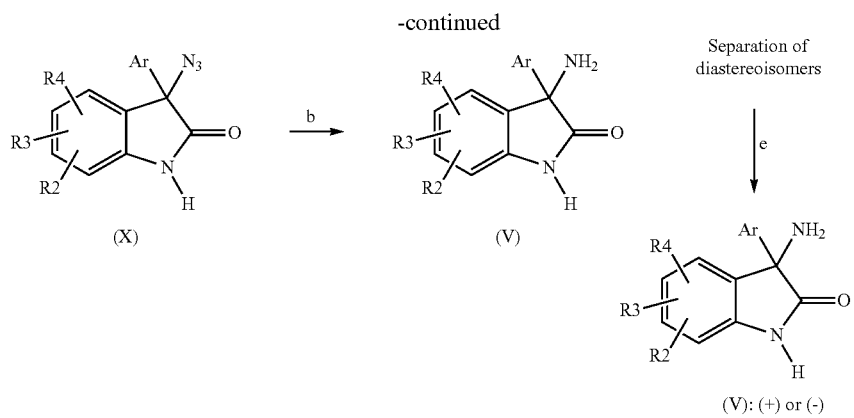

in which R2, R3, R4 and Ar are as defined in the general formula (I) and Hal represents a halogen atom, for example chlorine.

In step c of Scheme 2, the compound of formula (V) is prepared from a compound of formula (VIII) by sparging with ammonia gas according to the method described in patent application FR 2 714 378.

It is also possible to prepare the same compound via reduction of a compound of formula (X) according to methods known to those skilled in the art, for example by means of zinc in a solvent such as methanol. The preparation of a compound of formula (X) of the step is described in patent application FR 2 714 378.

An optically pure compound of formula (V) may be synthesized according to steps d and e of Scheme 3, as described in patent application WO 03/008 407.

The intermediates of general formula (VIII) may be prepared according to the processes described in patent application WO 03/008 407 and illustrated by Scheme 3:

Scheme 3:

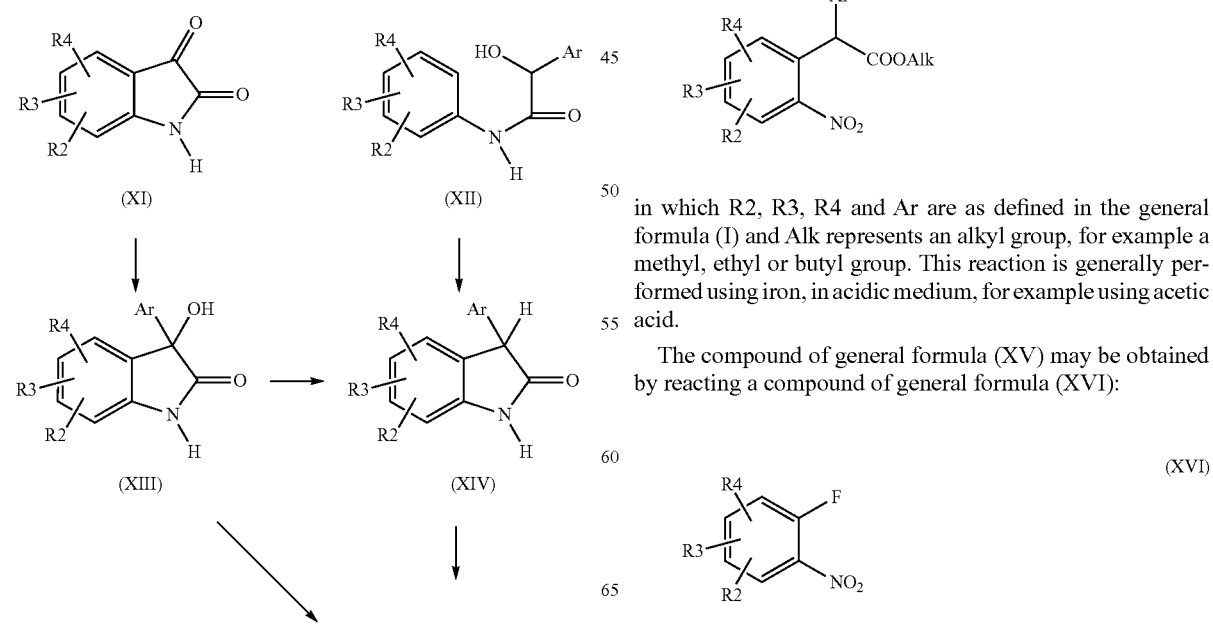

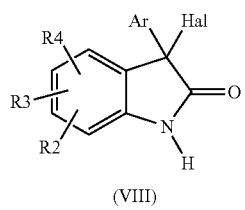

in which R2, R3, R4 and Ar are as defined in the general formula (I) and Hal represents a halogen atom, for example chlorine.

The compounds of general formula (XIV) may also be prepared by application or adaptation of the procedures described in the *Journal of Heterocyclic Chemistry*, 43(4), 1031-1035; 2006.

Thus, the compounds of general formula (XIV) may be prepared by reducing a compound of formula (XV):

in which R2, R3, R4 and Ar are as defined in the general formula (I) and Alk represents an alkyl group, for example a methyl, ethyl or butyl group. This reaction is generally performed using iron, in acidic medium, for example using acetic acid.

The compound of general formula (XV) may be obtained by reacting a compound of general formula (XVI):

in which R2, R3 and R4 are as defined in the general formula (I), with a compound of formula (XVII):

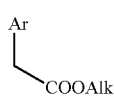

(XVII)

in which Ar is as defined in the general formula (I) and Alk represents an alkyl group, for example a methyl, ethyl or butyl group, according to methods known to those skilled in the art and described in the *Journal of Heterocyclic Chemistry*, 43(4), 1031-1035; 2006, for example in the presence of a base such as t-BuOK or NaH.

The compound of general formula (VII) may be prepared according to one or other of the following methods, illustrated by Scheme 4:

Scheme 4:
1) X = ―CH<

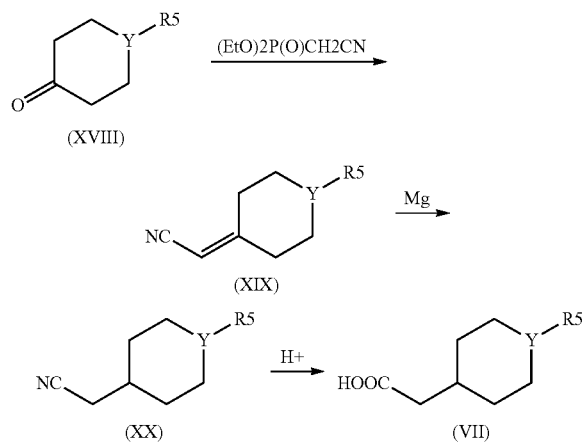

2) X = ―N<

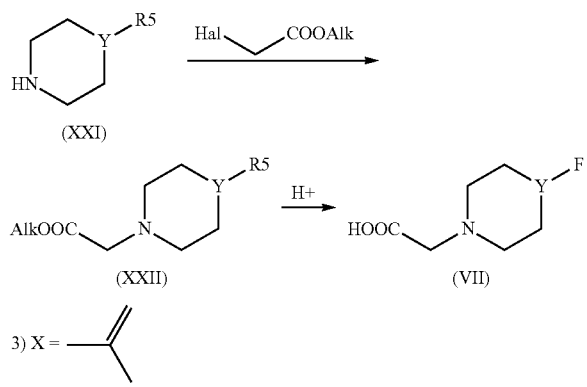

3) X =
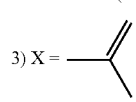

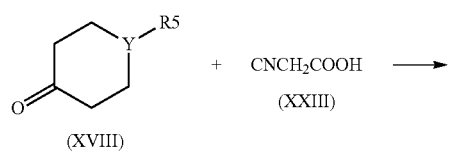

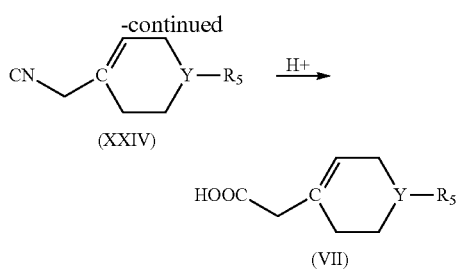

According to the first embodiment, when X=—CH<, the compound of formula (VII) may be prepared by hydrolysis of a compound of formula (XX):

(XX)

in which R5 and Y are defined as in the general formula (I), in acidic medium, for example using concentrated hydrochloric acid.

The compound of general formula (XX) may be prepared by reducing a compound of formula (XIX):

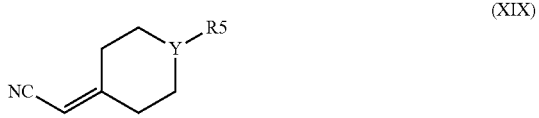

(XIX)

in which R5 and Y are defined as in the general formula (I), for example using magnesium. This reaction is generally performed in a solvent such as methanol or ethanol.

The compound of general formula (XIX) may be prepared via a Wittig-Horner reaction starting with the compound of general formula (XVIII):

(XVIII)

in which R5 and Y are defined as in the general formula (I). Generally, this reaction is performed using a suitable phosphonate derivative, such as diethyl (cyanomethyl)phosphonate. The process is advantageously performed in the presence of a base, such as $K_2CO_3$, in a solvent such as THF or dimethoxyethane.

According to the second embodiment, when X=—N<, the compound of formula (VII) may be prepared from a compound of formula (XXII):

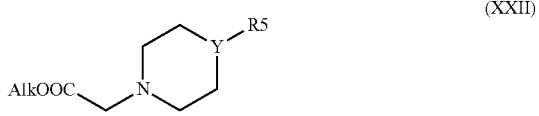

(XXII)

in which R5 and Y are defined as in the general formula (I), and Alk represents an alkyl group, for example a methyl, ethyl or butyl group. This reaction is generally performed in acidic medium, for example using concentrated hydrochloric acid.

The compound of general formula (XXII) may be prepared by condensation of a compound of general formula (XXI):

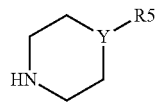
(XXI)

in which R5 and Y are defined as in the general formula (I), with a corresponding halo compound, such as Hal′′′CH$_2$COOAlk, in which Hal′′′ represents a halogen atom such as chlorine and Alk represents an alkyl group, such as ethyl. This reaction is advantageously performed in a solvent such as toluene, benzene or dioxane.

According to the third embodiment, when X=

the compound of formula (VII) may be prepared by hydrolysis of a compound of formula (XXIV):

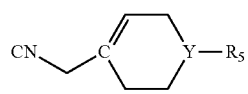
(XXIV)

in which R5 and Y are defined as in the general formula (I), in acidic medium, for example using concentrated hydrochloric acid.

The compound of general formula (XXIV) may be prepared by reaction starting with the compound of general formula (XVIII):

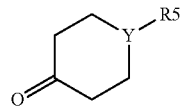
(XVIII)

in which R5 and Y are defined as in the general formula (I), using the compound of general formula (XXIII):

NC—CH$_2$COOH   (XXIII)

Generally, this reaction is performed in a solvent such as THF.

According to another embodiment, the compounds of general formula (I) in which R1 represents an alkyl group and R2, R3, R4, R5, Ar, X, Y and n are as defined in the general formula (I) may also be prepared according to Scheme 5 below:

Scheme 5:

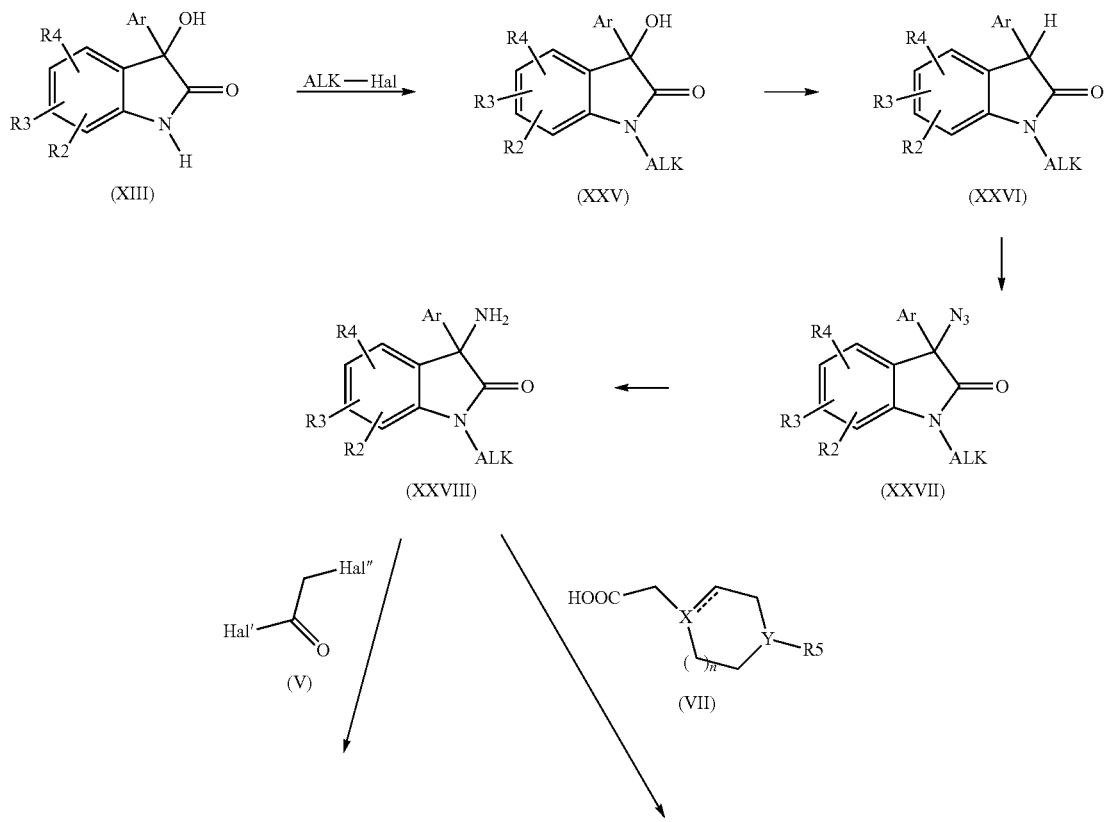

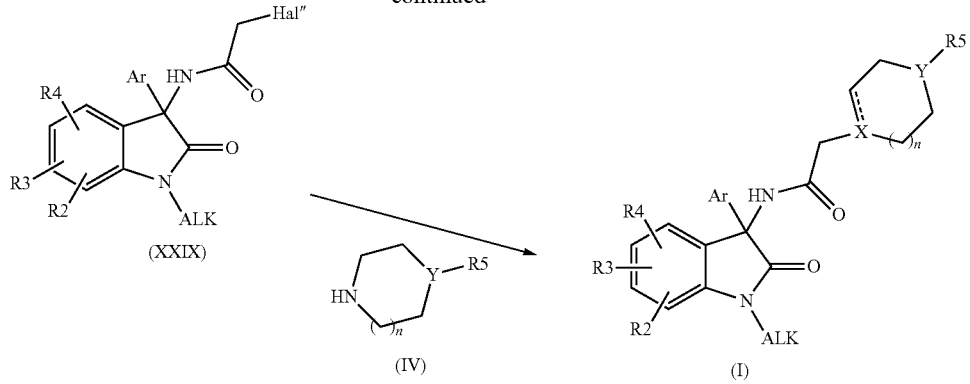

The compound of general formula (XXV) may be prepared by reacting a compound of formula (XIII) with a compound of formula (XIV):

ALK-Hal (XIV)

in which ALK represents a linear or branched saturated aliphatic group containing from 1 to 6 carbon atoms and Hal represents a halogen atom, for example chlorine, according to methods known to those skilled in the art, for example in the presence of a base such as $K_2CO_3$, NaH or t-BuO$^-$K$^+$ in a solvent such as DMF, THF, dimethoxyethane or DMSO.

The compounds of general formula (XXVIII) may be prepared according to methods analogous to those described previously.

The compounds of general formula (XXVIII) may also be prepared according to Scheme 6 below:

Scheme 6:

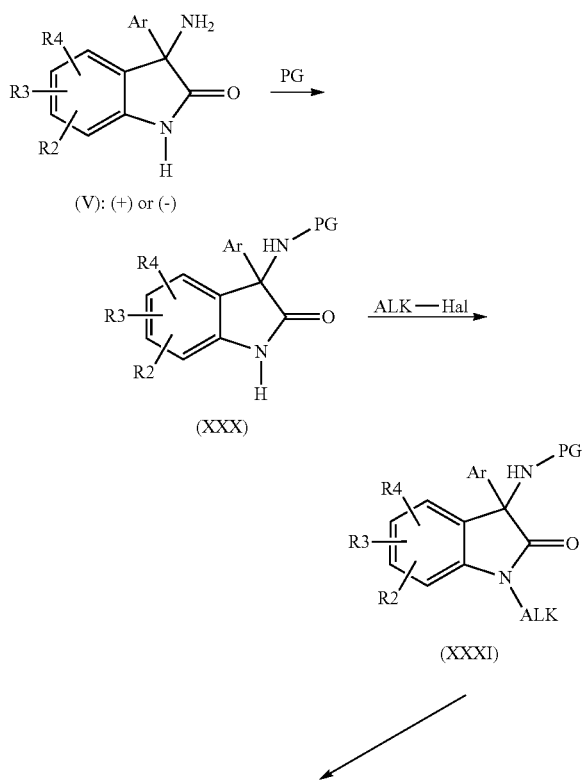

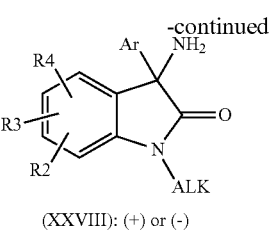

According to this scheme, a compound of formula (V) is reacted with a protecting group PG to give the compound of formula (XXX). Examples of protecting groups PG for the amine that may be used include benzimine and t-butyl carbamate. These protecting groups are introduced according to methods known to those skilled in the art, for example in the presence of a base such as $K_2CO_3$, NaOH or triethylamine, in a solvent such as dioxane, THF or DMSO.

The compound of general formula (XXXI) may be prepared by reacting a compound of formula (XXX) with a compound of formula (XIV)

ALK-Hal (XIV)

in which ALK represents a linear or branched saturated aliphatic group containing from 1 to 6 carbon atoms and Hal represents a halogen atom, for example chlorine.

The compound of general formula (XXVIII) is obtained from a compound of formula (XXXI) by removing the protecting group according to well-known methods, for example in acidic medium with HCl or trifluoroacetic acid.

By then working by application of the methods described above for the compounds of general formulae (XIII), (XIV), (X), (V), (III) and (I) of Schemes 1, 2 and 3, the compounds of general formulae (XXV), (XXVI), (XXVII), (XXVIII), (XXIX) and (I) are obtained.

Optionally, the compound of formula (I) is converted into an acid-addition salt thereof.

The process according to the invention may optionally include the step that consists in isolating the desired product of general formula (I).

In Schemes 1, 2, 3, 4, 5 and 6, the starting materials and the reagents, when their mode of preparation is not described, are commercially available or described in the literature, or else may be prepared according to methods that are described therein or that are known to those skilled in the art.

According to another of its aspects, a subject of the invention is also the compounds of formula (III), with the exclusion of 5-chloro-3-(2-chloro-acetamido)-3-(2-chlorophenyl)-1,3-dihydroindol-2-one. These compounds are useful as synthetic intermediates for the compounds of formula (I).

Among the compounds of formula (III) that are subjects of the invention, one group of compounds is constituted by the compounds for which:

Ar represents a heteroaryl group optionally substituted with one or more substituents, which may be identical or different, chosen from halogen atoms and (C1-6)alkyl, perhalo(C1-3)alkyl, (C1-6)alkoxy and aryl groups.

According to another of its aspects, a subject of the invention is also the compounds of formulae (XXVIII) and (XXIX). These compounds are useful as synthetic intermediates for the compounds of formula (I).

The examples that follow describe the preparation of certain compounds in accordance with the invention. These examples are not limiting, and serve merely to illustrate the present invention. The numbers of the illustrated compounds refer to those given in the table hereinbelow, which illustrates the chemical structures and the physical properties of a few compounds according to the invention.

The physicochemical measurements were performed in the following manner:

The melting points were measured using a Büchi B-540 machine.

The proton nuclear magnetic resonance ($^1$H NMR) spectra were recorded at 500 MHz on a Brüker machine equipped with an Avance III console. The chemical shifts are given in ppm relative to the frequency of TMS.

All the spectra were recorded at a temperature of 40° C.

The abbreviations used to characterized the signals are as follows:
s=singlet, bs=broad singlet, m=multiplet, d=doublet, t=triplet, q=quartet.
*=not integratable due to interference with a broad peak resulting from water.
**=not integratable due to interference with a peak resulting from the NMR solvent.

The HPLC was performed using a ThermoElectron Surveyor system equipped with an ion-trap mass spectrometry detector and a diode array detector.

The analysis conditions by liquid chromatography coupled to mass spectrometry (LC/UV/MS) are as follows:

For the liquid chromatography part, three different chromatographic systems are used:
chromatographic system A
Eluent A=H$_2$O+0.005% TFA
Eluent B=CH$_3$CN
gradient from 95% A to 90% B over 17 minutes, followed by elution with 90% B for 5 minutes
flow rate 0.3 ml/minute
injection of 2 μL of solution at 0.1 mg/ml in a 9/1 CH$_3$CN/H$_2$O mixture
chromatographic system B
Eluent A=H$_2$O+0.01% TFA
Eluent B=CH$_3$CN
gradient from 98% A to 95% B over 10 minutes, followed by elution with 95% B for 5 minutes
flow rate 0.5 ml/minute; temperature 40° C.
injection of 2 μL of solution at 0.1 mg/ml in a 9/1 CH$_3$CN/H$_2$O mixture
chromatographic system C
Eluent A=H$_2$O+0.005 M ammonium acetate pH 6.5
Eluent B=CH$_3$CN
gradient from 95% A to 90% B over 17 minutes, followed by elution with 90% B for 5 minutes
flow rate 0.3 ml/minute
injection of 2 μL of solution at 0.1 mg/ml in a 9/1 CH$_3$CN/H$_2$O mixture The columns used are:
Waters XTerra MS C18 2.1×50 mm 3.5 μm column No. 186000400
Waters XBridge C18 2.1×50 mm 2.5 μm column No. 186003085
Phenomenex Gemini C18 2.1×100 mm 510 μm column No. 00D-4435-B0
Waters Sunfire C18 2.1×100 mm 3.5 μm column No. 186002534.

The products are detected by UV at 220 nm.

For the mass spectrometry part:
ionization mode: positive electrospray (API-ES polarity+) scanning from 100 to 1200 amu.

Thin layer chromatography was performed on silica gel TLC plates from Merck. The silica gel for the flash column chromatography is sold by Biotage.

All the solvents used are of "reagent grade" or "HPLC grade" purity.

The αD measurements were carried out on a Perkin Elmer model PE341 polarimeter using a cell with a 1 dm optical path.

In the examples and preparations:
AcOH and EtOAc represent, respectively, acetic acid and ethyl acetate.
MeOH, EtOH and t-BuOH represent, respectively, methanol, ethanol and tert-butanol.
m.p. means melting point.

PREPARATION 1

(1-Methylpiperid-4-yl)acetic acid (i) (1-Methylpiperid-4-ylidene)acetonitrile 9.36 g of K$_2$CO$_3$ and 8.89 ml of diethyl (cyanomethyl)phosphonate are placed in 12 ml of THF in a round-bottomed flask equipped with a magnetic stirrer, and under a stream of nitrogen, and the mixture is left to react for 15 minutes at room temperature and then refluxed for 20 minutes. The resulting mixture is allowed to cool and 6.5 ml of 1-methyl-4-piperidone are added dropwise. This mixture is refluxed for 16 hours. The reaction mixture is then poured into water and extracted with ethyl acetate. The organic phase is dried over Na$_2$SO$_4$, filtered and evaporated under vacuum. 6.8 g of oil are obtained.

(ii) (1-Methylpiperid-4-yl)acetonitrile 1 g of the product obtained in the preceding step is placed in 70 ml of methanol in a round-bottomed flask equipped with a magnetic stirrer. At 0° C., 7.2 g of magnesium are added portionwise. The mixture is stirred for 4 hours. It is filtered to remove the solid magnesium particles and the filtration and liquors are evaporated. The residue is taken up in saturated NaCl solution and extracted with dichloromethane. The organic phase is dried over Na$_2$SO$_4$, filtered and evaporated under vacuum. 450 mg of oil are obtained.
TLC: 9/1 EtOAc/MeOH, Rf=0.2

(iii) (1-Methylpiperid-4-yl)acetic acid 3.65 g of the product obtained in step (ii) are placed in 47 ml of concentrated hydrochloric acid in a round-bottomed flask equipped with a magnetic stirrer. The mixture is refluxed for 20 hours. The resulting mixture is diluted with water and extracted with dichloromethane to remove the impurities. The aqueous phase is brought to pH 5-6 and extracted with dichloromethane. The aqueous phase is evaporated under vacuum and a white solid is isolated. This solid is taken up in ethanol to separate the product from the salts. The filtration liquors are evaporated to isolate 3.6 g of pale yellow solid.
TLC: 99/1 MeOH/NH$_4$OH, Rf=0.2

PREPARATION 2

(1-Ethylpiperid-4-yl)acetic acid

By working as described in Preparation 1, but using 1-ethyl-4-piperidone instead of 1-methyl-4-piperidone, the title compound is obtained.
TLC: 100% MeOH, Rf=0.15.

PREPARATION 3

(4-Ethylpiperazin-1-yl)acetic acid (i) Ethyl (4-ethylpiperazin-1-yl)acetate 8.9 ml of ethylpiperazine are placed in 91.5 ml of toluene in a round-bottomed flask. A solution of 4.1 ml of ethyl bromoacetate in 11.6 ml of toluene is added dropwise. The mixture is refluxed at 110° C. for one hour, concentrated to a small volume and left in a refrigerator for 3 hours. A white precipitate forms, which is filtered off and washed with dichloromethane. The filtration liquors are evaporated; 7 g of expected product are obtained.
TLC: 1/1 EtOAc/MeOH, Rf=0.45.

(ii) (4-Ethylpiperazin-1-yl)acetic acid 7 g of the product obtained in the preceding step are added to 190 ml of 6N HCl and the mixture is refluxed for 4 hours. It is evaporated to dryness and washed with a 1/1 EtOAc/EtOH mixture, and the white solid obtained is dried. 7 g of expected product are obtained.
TLC: 100% MeOH, Rf=0.2.

PREPARATION 4

(4-Methylpiperazin-1-yl)acetic acid

By working as described in Preparation 3, but using 1-methylpiperazine instead of 1-ethylpiperazine, the title compound is obtained.
TLC: 100% MeOH, Rf=0.25.

PREPARATION 5

(+)-3-Amino-5,6-dichloro-1,3-dihydro-3-(4-chlorophenyl)indol-2-one (i) 5,6-dichloro-1,3-dihydro-3-(4-chlorophenyl)indol-2-one A) Methyl (4-chlorophenyl)(4,5-dichloro-2-nitrophenyl)acetate A solution of 5 g of 1,2-dichloro-4-fluoro-5-nitrobenzene and 4.4 g of methyl 4-chlorophenylacetate in 70 ml of DMF is added, under a stream of nitrogen, to a suspension at −10° C. of 2.85 g of 60% NaH in 45 ml of DMF, and the temperature is maintained at −5° C. The mixture is reacted for 2 hours, while allowing the temperature to return to room temperature. The resulting mixture is poured onto ice, aqueous 10% NH$_4$Cl solution is added and the mixture is extracted with ethyl acetate. The organic phase is dried, filtered and concentrated. 30 g of a brown oil are obtained, and are purified on a column with hexane and then with a 95/5 hexane/EtOAc mixture to give 3.18 g of oil.

B) 5,6-dichloro-1,3-dihydro-3-(4-chlorophenyl)indol-2-one 4.6 g of the product from step A, 60 ml of methanol, 15 ml of AcOH and 2.7 g of iron are placed in a round-bottomed flask equipped with a mechanical stirrer, under a stream of nitrogen, and the mixture is refluxed for 1 hour 30 minutes. The resulting mixture is poured onto ice and 10% NaHCO$_3$ solution is added to basic pH. Ethyl acetate is added and the mixture is filtered. The organic phase is separated out and dried, filtered and concentrated. A solid is obtained, which is taken up in isopropyl ether and filtered. 2.75 g of a white solid are obtained.
m.p.: 214-215° C.

(ii) 5,6-dichloro[[(1R)-2-hydroxy-1-phenylethyl]amino]-1,3-dihydro-3-(4-chloro-phenyl)indol-2-one isomer A and isomer B A) 3-bromo-5,6-dichloro-1,3-dihydro-3-(4-chlorophenyl)indol-2-one 2.75 g of the product from step B above are dissolved in 100 ml of dichloromethane under a stream of nitrogen. The solution is cooled in an ice bath, and a solution of 3.93 g of PhMe$_3$NBr$_3$ in 100 ml of dichloromethane is added dropwise. The mixture is reacted for 3 hours, and the temperature is allowed to return gradually to room temperature. The resulting mixture is washed with 1M hydrochloric acid and water. This mixture is dried, filtered and concentrated. 3.7 g of oil are obtained.

B) 5,6-dichloro[[(1R)-2-hydroxy-1-phenylethyl]amino]-1,3-dihydro-3-(4-chloro-phenyl)indol-2-one isomer A and isomer B 3.4 g of the compound from the preceding step are mixed with 50 ml of chloroform and 2.9 g of R-phenylglycinol, under a stream of nitrogen. The mixture is reacted for 2 hours at room temperature, 1.6 ml of DIPEA are then added and the resulting mixture is reacted at room temperature. The solid formed is filtered off, and the filtration liquors are evaporated to dryness and purified on a column, eluting with 7/3 hexane/EtOAc.
1.8 g of the less polar product, isomer A (m.p.=79.8-80.5° C.) and 2.2 g of the more polar isomer B (m.p.=213.2° C.) are obtained.

(iii) (+)-3-Amino-5,6-dichloro-1,3-dihydro-3-(4-chlorophenyl)indol-2-one 1.8 g of the product obtained in the preceding step are reacted in a mixture of 28 ml of dichloromethane and 12 ml of methanol. 1.9 g of Pb(OAc)$_4$ are added and the mixture is reacted at room temperature for 3 hours. The resulting mixture is evaporated to dryness and the residue is taken up in ethyl acetate and then washed with saturated aqueous NaHCO$_3$ solution. The organic phase is dried, filtered and concentrated. The resulting product is taken up in a mixture of 36 ml of 3N hydrochloric acid and 3.7 ml of methanol, and is stirred overnight. This mixture is concentrated and diluted with a mixture of water and dichloromethane. The organic phase is washed with 1N hydrochloric acid solution. The aqueous phases are combined, brought to basic pH with aqueous NH$_3$ solution and extracted with dichloromethane. The organic phase is dried, filtered and concentrated to give 540 mg of a white solid product.

m.p.=221° C.; α$_D$=+32.5°, c=0.5 wt % MeOH

PREPARATION 6

(−)-3-Amino-5,6-dichloro-1,3-dihydro-3-(4-chlorophenyl)indol-2-one

By working as described in Preparation 5 (iii), but using the more polar isomer B obtained in Preparation 5 (ii) instead of isomer A of the same preparation, the title compound is obtained.

α$_D$=−23.6°, c=0.35 wt % MeOH.

PREPARATION 7

3-Amino-4,6-dichloro-1,3-dihydro-3-(4-chlorophenyl)indol-2-one (i) 4,6-dichloro-1,3-dihydro-3-(4-chlorophenyl)indol-2-one a) 4-chloro-O-acylmandelic chloride 10 g of 4-chloro-dl-mandelic acid, 88 ml of dichloromethane and 4.2 ml of acetyl chloride are placed in a two-necked round-bottomed flask equipped with a magnetic stirrer. The mixture is reacted at 50° C. for 3 hours. 7.8 ml of thionyl chloride are then added. The mixture is reacted at reflux for 2 hours. The resulting mixture is evaporated under vacuum to give 13.7 g of an opaque liquid.

b) 4-chloro-N-3,5-phenylmandelamide 4.04 g of 3,5-dichloroaniline and 50 ml of toluene are placed in a three-necked round-bottomed flask equipped with a mechanical stirrer, and under a stream of nitrogen. The solution is cooled to 0° C. 9.6 g of potassium carbonate are then added. 6.8 g of the product obtained in the preceding step diluted in 10 ml of toluene are added slowly. The mixture is reacted at room temperature for one hour, and 4.15 ml of methanol are then added. The mixture is reacted at 80° C. for 2 hours, followed by addition of 1N hydrochloric acid solution, and the resulting mixture is extracted with ethyl acetate. The organic phase is evaporated under vacuum. 5.7 g of solid are obtained.

c) 4,6-dichloro-1,3-dihydro-3-(4-chlorophenyl)indol-2-one 22 ml of 96% sulfuric acid and 5 ml of fuming sulfuric acid are placed in a round-bottomed flask equipped with a magnetic stirrer. The mixture is cooled in an ice bath; and 5.7 g of the product obtained in the preceding step are added portionwise. The mixture is then left to react at room temperature for 4 hours. The reaction is poured into a bath of ice and brought to basic pH with NaHCO$_3$ solution and then with concentrated sodium hydroxide solution. The resulting mixture is extracted with dichloromethane, and the organic phase is separated out, dried over Na$_2$SO$_4$, filtered and evaporated under vacuum to give 7.5 g of a solid, which is taken up in ethyl ether. This mixture is filtered to give 4.2 g of powder.

(ii) 3-Azido-4,6-dichloro-1,3-dihydro-3-(4-chlorophenyl)indol-2-one

A) 3-bromo-4,6-dichloro-1,3-dihydro-3-(4-chlorophenyl)indol-2-one

This product is obtained by working as described in point (ii) of Preparation 5, but using the compound obtained in the preceding step.

B) 3-azido-4,6-dichloro-1,3-dihydro-3-(4-chlorophenyl)indol-2-one 550 mg of the compound obtained in the preceding step, 17 ml of acetonitrile and 270 mg of NaN$_3$ are placed in a three-necked round-bottomed flask equipped with a mechanical stirrer, and under a stream of nitrogen. The mixture is refluxed for 2 hours and then taken up in ethyl acetate and washed with saturated sodium chloride solution. The organic phase is separated out, dried over Na$_2$SO$_4$, filtered and evaporated under vacuum to give 320 mg of a resin, which is purified by flash chromatography, eluting with 85/15 cyclohexane/ethyl acetate. The phase containing the product is evaporated to give 220 mg of a white solid.

(iii) 3-Amino-4,6-dichloro-1,3-dihydro-3-(4-chlorophenyl)indol-2-one 220 mg of the product obtained in the preceding step, 5 ml of THF, 10 ml of methanol, 170 mg of NH$_4$Cl and 80 mg of zinc are placed in a two-necked round-bottomed flask equipped with a mechanical stirrer. The mixture is reacted at room temperature for 3 hours. The resulting mixture is filtered and the residue is evaporated under vacuum. The resulting residue is taken up in ethyl acetate and washed with saturated sodium chloride solution. The organic phase is separated out, dried over Na$_2$SO$_4$, filtered and evaporated under vacuum. 200 mg of oil are obtained, which product is purified by flash chromatography, eluting with 8/2 cyclohexane/ethyl acetate. 74 mg of expected product are obtained.

TLC: 6/4 cyclohexane/EtOAc, Rf=0.3

PREPARATION 8

(+)-3-Amino-4,6-dichloro-1,3-dihydro-3-(4-trifluoromethylphenyl)indol-2-one (i) 3-Hydroxy-4,6-dichloro-1,3-dihydro-3-(4-trifluoromethylphenyl)indol-2-one 1.8 g of Grignard magnesium are placed in 19 ml of anhydrous ethyl ether in a round-bottomed flask equipped with a mechanical stirrer, and under a stream of nitrogen. A mixture of 8.9 ml of 4-bromotrifluoromethylbenzene in 46 ml of anhydrous ethyl ether is then added. The mixture is stirred for one hour, followed by addition of a solution of 5.7 g of 4,6-dichloro-1H-indole-2,3-dione in 100 ml of anhydrous THF. The mixture is stirred at room temperature for 4 hours 30 minutes. Water is added and the resulting mixture is extracted with ethyl acetate. The organic phase is separated out and dried over Na$_2$SO$_4$, filtered and evaporated under vacuum. The residue is taken up in ethyl acetate and washed with 1N sodium hydroxide solution. The organic phase is dried over Na$_2$SO$_4$, filtered and evaporated under vacuum. The solid is taken up in ethyl ether and filtered off. 4.7 g of expected product are obtained.

(ii) 3,5,6-trichloro-1,3-dihydro-3-(4-trifluoromethylphenyl)indol-2-one 1.2 g of the product from the preceding step are placed in 8 ml of dichloromethane in a round-bottomed flask equipped with a magnetic stirrer, and under a stream of nitrogen. 0.47 ml of pyridine and a mixture of 0.34 ml of $SOCl_2$ in 4 ml of dichloromethane are added, at 0° C. The mixture is reacted at room temperature and then poured into saturated aqueous $NH_4Cl$ solution. The organic phase is separated out and dried over $Na_2SO_4$, filtered and evaporated under vacuum.

TLC: 1/1 hexane/EtOAc, Rf=0.85

(iii) 4,6-dichloro[[(1S)-2-hydroxy-1-phenylethyl]amino]-1,3-dihydro-3-(4-trifluoromethylphenyl)indol-2-one isomer A and isomer B By working as described in step (ii) A and B of Preparation 5, but using the compound from the preceding step and (S)-phenylglycinol instead of (R)-phenylglycinol, the title compounds are obtained.

TLC: 4/6 EtOAc/cyclohexane, Rf=0.5 (isomer A), Rf=0.2 (isomer B)

(iv) (+)-3-Amino-5,6-dichloro-1,3-dihydro-3-(4-trifluoromethylphenyl)indol-2-one This compound is obtained by working as described in step (ii) B of Preparation 5.

$\alpha_D$=+60°, c=0.25 wt % in MeOH

PREPARATION 9

3-Amino-1,5-dimethyl-6-chloro-1,3-dihydro-3-(4-chlorophenyl)indol-2-one

(i) 6-Chloro-3-(4-chlorophenyl)-3-hydroxy-1,5-dimethyl-1,3-dihydroindol-2-one This compound is prepared from 3-hydroxy-5-methyl-6-chloro-1,3-dihydro-3-(4-chlorophenyl)indol-2-one (compound obtained according to the process described in point (i) of Preparation 8), and 1.2 g thereof are dissolved in 8 ml of DMF. 167 mg of 60% NaH are added at 0° C., under a stream of nitrogen. 260 µl of $CH_3I$ are then added and the mixture is reacted for 30 minutes. The resulting mixture is poured into water and extracted with dichloromethane. The organic phase is dried, filtered and concentrated. The product is purified on a column, eluting with 9/1 hexane/EtOAc.

TLC: 1/1 EtOAc/hexane, Rf=0.7

(ii) 6-Chloro-3-(4-chlorophenyl)-1,5-dimethyl-1,3-dihydroindol-2-one 1 g of the product obtained from the preceding step is mixed with 4 ml of TFA and 1.3 ml of $HSiEt_3$, and the mixture is reacted for one hour at 80° C. The resulting mixture is poured into water and brought to basic pH with aqueous $NH_3$ solution. This mixture is extracted with ethyl acetate. The organic phase is dried, filtered and concentrated. The residue is taken up in ethyl ether and filtered. 688 mg of a white solid are obtained.

TLC: 4/6 EtOAc/hexane, Rf=0.7

(iii) 3-Amino-1,5-dimethyl-6-chloro-1,3-dihydro-3-(4-chlorophenyl)indol-2-one by working as described in Preparation 7 in points (ii) and (iii), but using the product from the preceding step instead of the product obtained in step (i) of Preparation 7, the title compound is obtained.

TLC: 1/1 EtOAc/hexane, Rf=0.5

PREPARATION 10

(1-Ethyl-1,2,3,6-tetrahydropyrid-4-yl)acetic acid

(i) (1-ethyl-1,2,3,6-tetrahydropyrid-4-yl)acetonitrile 2.9 g of 1-ethyl-4-piperidone, 3.3 g of cyanoacetic acid and 36 ml of toluene are placed in a round-bottomed flask equipped with a magnetic stirrer, and under a stream of nitrogen. The mixture is refluxed for 4 hours, while removing the water using Markusson apparatus. The solvent is evaporated off under vacuum. 4.2 g of oil are obtained.

(ii) (1-Ethyl-1,2,3,6-tetrahydropyrid-4-yl)acetic acid

By working as described in Preparation 1 (iii), but using the product from the preceding step instead of the product of Preparation 1 (ii), the title compound is obtained.

TLC: 99/1 MeOH/$NH_4OH$, Rf=0.2
$^1$H NMR: δ (ppm, DMSO-d6): 1.09 (t, J=7.2 Hz, 3H), 2.18 (m, 2H), 2.62 (q, J=7.2 Hz, 2H), 2.68-2.76 (m, 2H), 2.92 (s, 2H), 3.11 (bs, 2H), 5.49 (m, 1H).

PREPARATION 53

(+)-3-amino-1-isopropyl-4,6-dichloro-1,3-dihydro-3-(3,4-dichlorophenyl)-indol-2-one

(i) (+)-3-amino-4,6-dichloro-1,3-dihydro-3-(3,4-dichlorophenyl)indol-2-one

The compound is obtained by working as described in Preparation 5, but using in step (i) 3,4-dichlorobromobenzene instead of 4-bromotrifluoromethyl-benzene.

(ii) (+)-3-benzimino-4,6-dichloro-1,3-dihydro-3-(3,4-dichlorophenyl)indol-2-one 215 mg of the product obtained in the preceding step and 120 µl of benzaldehyde are placed in a round-bottomed flask. The mixture is heated at 100° C. for 5 minutes in a microwave reactor. A solid is obtained, which is dried under vacuum to remove the benzaldehyde.

(iii) (+)-3-benzimino-1-isopropyl-4,6-dichloro-1,3-dihydro-3-(3,4-dichloro-phenyl)indol-2-one 144 mg of the product obtained in the preceding step are placed in DMF (800 µl) in the presence of $K_2CO_3$ (49 mg) and isopropyl bromide (30 µl) in a round-bottomed flask. The mixture is heated at 140° C. for 5 minutes in a microwave reactor. The resulting mixture is filtered and the crude product is used for the following step.

(iv) (+)-3-amino-1-isopropyl-4,6-dichloro-1,3-dihydro-3-(3,4-dichlorophenyl)-indol-2-one The product obtained in the preceding step (157 mg) is dissolved in methanol (550 µl) and 2.7 ml of a 3N HCl solution are added. After 5 hours at room temperature, the mixture is neutralized with aqueous ammonia and extracted with ethyl acetate. The extracts are dried and evaporated. A semisolid product (112 mg) is obtained.

The following intermediates of general formula (V) in which R1, R2, R3, R4 and Ar are as defined in Table 1 were also prepared via the methods used for Preparations 5, 6, 7, 8 and 9.

Table 1 that follows illustrates the chemical structures and the physical properties of a few preparations according to the invention. In this table:

in the "isomer" column, "rac" represents a racemic mixture, and (+) or (−) represents one or other of the stereoisomers, Me, Et, n-Pr, i-Pr, n-Bu and i-Bu represent, respectively, methyl, ethyl, n-propyl, isopropyl, n-butyl and isobutyl groups, and Ph and Bn represent, respectively, phenyl and benzyl groups.

TABLE 1

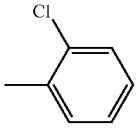

| Preparation | Ar | R2 | R3 | R4 | Isomer | Analyses |
|---|---|---|---|---|---|---|
| 11 | 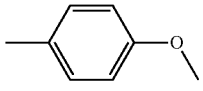 | 6-Cl | 5-ME | H | rac | $(M + H)^+ = 307$ |
| 12 |  | 6-Cl | 5-Cl | H | rac | 1/1 cyclohexane/EtOAc, Rf = 0.27 |
| 13 | 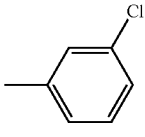 | 6-Cl | 5-Me | H | rac | 1/1 cyclohexane/EtOAc, Rf = 0.3 |
| 14 | 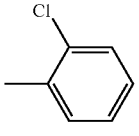 | 6-Cl | 5-Me | H | rac | 1/1 cyclohexane/EtOAc, Rf = 0.3 |
| 15 | 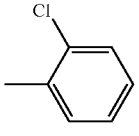 | 6-CF3 | H | H | rac | 1/1 cyclohexane/EtOAc, Rf = 0.3 |
| 16 | 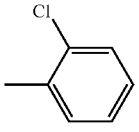 | H | 5-Me | 4-Cl | rac | m.p. = 220° C. $(M + H)^+ = 307$ |
| 17 | 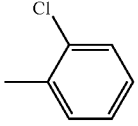 | H | 5-Me | 4-Me | rac | m.p. = 200° C. $(M + H)^+ = 287$ |
| 18 | 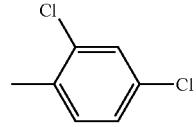 | 6-Cl | H | H | rac | m.p. = 251° C. $(M + H)^+ = 293$ |
| 19 |  | 6-Cl | 5-Me | H | rac | m.p. = 255° C. $M^- = 339$ |

TABLE 1-continued

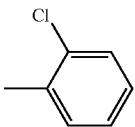

| Preparation | Ar | R2 | R3 | R4 | Isomer | Analyses |
|---|---|---|---|---|---|---|
| 20 | 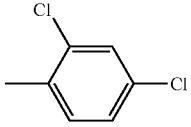 | H | 5-Me | H | rac | 1/1 cyclohexane/EtOAc, Rf = 0.3 |
| 21 | 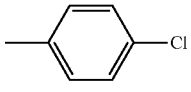 | 7-Br | 6-Cl | 5-Me | rac | 1/1 cyclohexane/EtOAc, Rf = 0.3 |
| 22 | 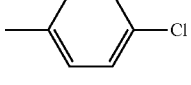 | 6-Cl | 5-Me | H | rac | 1/1 cyclohexane/EtOAc, Rf = 0.3 |
| 23 | 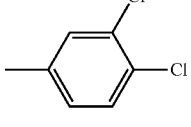 | H | 5-Me | 4-Cl | rac | 1/1 cyclohexane/EtOAc, Rf = 0.3 |
| 24 | 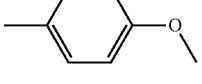 | 6-Cl | 5-Me | H | rac | 1/1 cyclohexane/EtOAc, Rf = 0.3 |
| 25 | 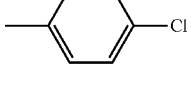 | 6-Cl | 5-Me | H | rac | 1/1 cyclohexane/EtOAc, Rf = 0.27 |
| 26 | 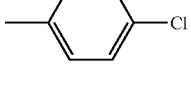 | 6-Me | 5-Cl | H | rac | 1/1 cyclohexane/EtOAc, Rf = 0.3 |
| 27 | 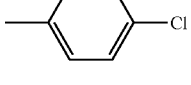 | 6-Cl | 5-Cl | H | rac | $(M + H)^+ = 327$ |
| 28 | 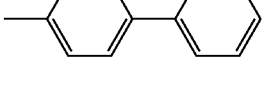 | 6-I | H | 4-CF3 | rac | 1/1 cyclohexane/EtOAc, Rf = 0.3 |
| 29 | 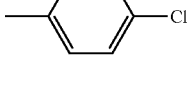 | 6-Cl | 5-Cl | H | rac | 1/1 hexane/EtOAc, Rf = 0.45 |
| 30 | 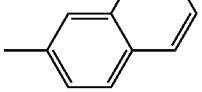 | 6-Cl | 5-Cl | 4-Cl | rac | m.p. = 246° C. $M^- = 359$ |
| 31 |  | 6-Cl | 5-Cl | H | rac | 1/1 hexane/EtOAc, Rf = 0.5 |

TABLE 1-continued

| Preparation | Ar | R2 | R3 | R4 | Isomer | Analyses |
|---|---|---|---|---|---|---|
| 32 | 4-Br-C6H4 | 6-Cl | 5-Cl | H | rac | (M + H)+ = 369 |
| 33 | 4-tBu-C6H4 | 6-Cl | 5-Cl | H | rac | 1/1 hexane/EtOAc, Rf = 0.45 |
| 34 | 4-Br-C6H4 | 6-Cl | 5-Cl | H | (−) | m.p. = 240° C. αD = −43°, c = 0.25% in MeOH |
| 35 | 4-Cl-C6H4 | 7-Cl | 6-H | 5-Cl | rac | 1/1 cyclohexane/EtOAc, Rf = 0.3 |
| 36 | 4-CN-C6H4 | 6-Cl | 5-Cl | H | rac | m.p. = 180° C. |
| 37 | 4-CF3-C6H4 | 6-Cl | 5-Cl | H | rac | 1/1 cyclohexane/EtOAc, Rf = 0.45 |
| 38 | 4-F-C6H4 | 6-Cl | 5-Cl | H | rac | 1/1 cyclohexane/EtOAc, Rf = 0.3 |
| 39 | 4-Cl-C6H4 | 6-CN | 5-H | 4-CF3 | rac | M− = 350 |
| 40 | 4-Br-C6H4 | 6-Cl | 5-H | 4-Cl | rac | 1/1 cyclohexane/EtOAc, Rf = 0.3 |
| 41 | 4-NO2-C6H4 | 6-Cl | 5-Cl | H | (+) | αD = +28°, c = 0.25% in MeOH |
| 42 | 4-Cl-C6H4 | 6-Cl | H | H | (+) | αD = +19°, C = 0.26% in MeOH |
| 43 | 4-Cl-C6H4 | 6-Cl | H | H | (−) | αD = −23°, c = 0.64% in MeOH |
| 44 | 4-CF3-C6H4 | 6-Cl | 5-H | 4-Cl | (+) | αD = +60°, c = 0.25% in MeOH |
| 45 | 4-Br-C6H4 | 6-Cl | 5-Cl | H | (+) | αD = +42°, c = 0.25% in MeOH |

TABLE 1-continued

| Preparation | Ar | R2 | R3 | R4 | Isomer | Analyses |
|---|---|---|---|---|---|---|
| 46 | 4-(N-acetyl)amino-phenyl | 6-Cl | 5-Cl | H | (+) | M⁻ = 348 |
| 47 | 4-bromophenyl | 6-F | 5-H | 4-F | (+) | α_D = +45°, c = 0.25% in MeOH<br>M⁻ = 339 |
| 48 | 4-chlorophenyl | 6-Cl | 5-H | 4-Cl | (+) | α_D = +99.2°, c = 0.5% in MeOH |
| 49 | 4-bromophenyl | 6-Cl | 5-H | 4-Cl | (+) | α_D = +92°, c = 0.25% in MeOH |
| 50 | 4-chlorophenyl | 6-Cl | 5-Me | H | (−) | αD = −91°, c = 0.16% in 3N HCl |
| 51 | 4-chlorophenyl | 6-Cl | 5-Me | H | (+) | αD = +104°, c = 0.16% in 3N HCl |
| 52 | 4-(trifluoromethyl)phenyl | 6-Cl | 5-Cl | H | (+) | m.p. = 231° C.<br>αD = +12.4°, c = 0.5% in MeOH |
| 53 | 4-bromophenyl | 6-CF3 | H | 4-Cl | (+) | αD = +88°, c = 20% in MeOH |
| 54 | 2-methyl-5-benzothienyl | 6-Cl | H | 4-Cl | (+) | (M + H)⁺ = 363 |
| 55 | 3-fluoro-4-chlorophenyl | 6-Cl | H | 4Cl | (+) | αD = +96°, c = 0.15% in MeOH |
| 54 | 5-benzofuranyl | 6-Cl | H | 4Cl | (+) | 6/4 hexane/EtOAc, Rf = 0.25 |
| 55 | 3,4-dichlorophenyl | 6-Cl | H | 4Cl | (+) | (M + H)⁺ = 361 |

TABLE 1-continued

| Preparation | Ar | R2 | R3 | R4 | Isomer | Analyses |
|---|---|---|---|---|---|---|
| 56 | 3,5-dichlorophenyl | 6-Cl | H | 4Cl | (+) | αD = +89°, c = 0.10% in MeOH |
| 57 | 2-chloro-5-(trifluoromethyl)phenyl | 6-Cl | H | 4Cl | (+) | αD = +79°, c = 0.10% in MeOH |
| 58 | 4-bromophenyl | 6-OMe | H | 4CF3 | (+) | αD = +62°, c = 0.50% in MeOH |
| 59 | 3,4-dichlorophenyl | 6-Cl | 5-F | 4Cl | rac | 7/1 cyclohexane/EtOAc, Rf = 0.4 |
| 60 | 3,4-dichlorophenyl | 6-Cl | H | 4Cl | rac | 7/1 cyclohexane/EtOAc, Rf = 0.4 |
| 61 | 2-methyl-5-benzofuranyl | 6-Cl | H | 4Cl | (+) | αD = +62°, c = 0.50% in MeOH |
| 62 | 4-chlorophenyl | 6-Br | H | H | (+) | (M − NH3)+ = 320 |
| 63 | 4-chlorophenyl | 6-phenyl | H | H | (−) | αD = −32°, c = 0.17% in MeOH |
| 64 | 3,4-dichlorophenyl | 6-Cl | H | H | (+) | (M − NH3)+ = 310 |
| 65 | 4-(trifluoromethoxy)phenyl | 6-Cl | H | 4Cl | (+) | (M + H)+ = 377 |

TABLE 1-continued
| Preparation | Ar | R2 | R3 | R4 | Isomer | Analyses |
|---|---|---|---|---|---|---|
| 66 | 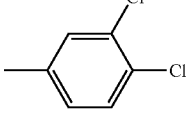 | 6-Br | H | H | rac | 6/4 hexane/EtOAc, Rf = 0.4 |
| 67 | 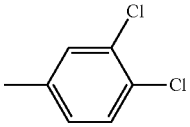 | 6-Br | H | H | (+) | 6/4 hexane/EtOAc, Rf = 0.4 |
| 68 | 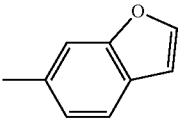 | 6-Cl | H | 4Cl | (+) | 1/1 hexane/EtOAc, Rf = 0.5 |
| 69 | 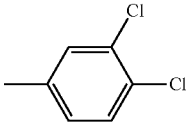 | 6-Cl | H | 4Cl | (+) | $(M + H)^+ = 359$ |
| 70 | 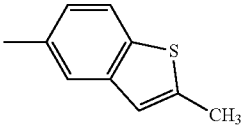 | 6-Cl | H | 4Cl | rac | $(M + H)^+ = 363$ |
| 71 | 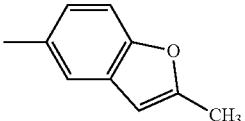 | 6-Cl | H | H | (+) | $(M + H)^+ = 313$ |
| 72 | 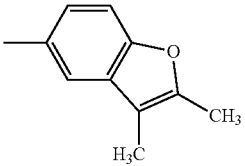 | 6-Cl | H | 4Cl | (+) | $(M + H)^+ = 361$ |
| 73 |  | 5-Br | H | H | (+) | $(M + H)^+ = 337$ |
| 74 | 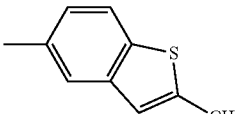 | 6-Br | H | H | (+) | $(M - NH_3)^+ = 356$ |
| 75 | 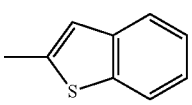 | 6-Cl | H | 4Cl | (+) | 7/3 dichloromethane/EtOAc, Rf = 0.85 |

TABLE 1-continued

| Preparation | Ar | R2 | R3 | R4 | Isomer | Analyses |
|---|---|---|---|---|---|---|
| 76 | 2-methylbenzothiazol-yl | 6-Cl | H | 4Cl | (+) | αD = +81°, c = 0.11 in MeOH |
| 77 | 2-methylbenzothiazol-yl | 6-Cl | H | 4Cl | (−) | αD = −82°, c = 0.10 in MeOH |
| 78 | 5-chloro-2-methylthien-yl | 6-Cl | H | 4Cl | (+) | αD = +154°, c = 0.25 in MeOH |
| 79 | 5-chloro-2-methylthien-yl | 6-Cl | H | 4Cl | (−) | αD = −216°, c = 0.25 in MeOH |
| 80 | 2,3-dichloro-4-methylpyridinyl | 6-Cl | H | 4Cl | (−) | αD = −116°, c = 0.10 in MeOH |
| 81 | 2-methylbenzothien-5-yl | 6-Cl | H | H | (+) | $(M + H)^+ = 327$ |
| 82 | 4-(trifluoromethoxy)phenyl | 6-Cl | H | H | (+) | $(M - NH_3)^+ = 326$ |
| 83 | 4-(trifluoromethoxy)phenyl | 6-Br | H | H | (+) | $(M + H)^+ = 385$ |
| 84 | 5-methylpyridin-2-yl | 6-Cl | H | H | rac | $(M + H)^+ = 274$ |

EXAMPLE 1

(+)-N-[5,6-Dichloro-3-(4-chlorophenyl)-2-oxo-2,3-dihydro-1H-indol-3-yl]-2-(4-methylpiperazin-1-yl)acetamide (i) 2-Chloro-N-[5,6-dichloro-3-(4-chlorophenyl)-2-oxo-2,3-dihydro-1H-indol-3-yl]acetamide 1.3 g of the product obtained in Preparation 5, 47 ml of toluene, 0.32 ml of pyridine and 0.31 ml of chloroacetyl chloride are placed in a round-bottomed flask equipped with a magnetic stirrer, and under a stream of nitrogen. The mixture is left to react at 110° C. for 4 hours, and the reaction mixture is then poured into water and extracted with ethyl acetate. The organic phase is dried over $Na_2SO_4$, filtered and evaporated under vacuum. 900 mg of a beige solid are obtained, which product is purified on a column by flash chromatography using an 8/2 cyclohexane/ethyl acetate mixture, to obtain 400 mg of the expected product.

TLC: 1/1 hexane/EtOAc, Rf=0.5

(ii) (+)-N-[5,6-Dichloro-3-(4-chlorophenyl)-2-oxo-2,3-dihydro-1H-indol-3-yl]-2-(4-methylpiperazin-1-yl)acetamide 0.4 g of the product from the preceding step, 0.11 ml of N-methylpiperazine (d 0.903), 0.14 g of potassium carbonate and 0.07 g of sodium iodide in 8 ml of DMF are placed in a round-bottomed flask equipped with a magnetic stirrer. The reaction mixture is left to react at 60° C. for 4 hours, and is then poured into water and extracted with ethyl acetate. The organic phase is dried over $Na_2SO_4$, filtered and evaporated under vacuum. 240 mg of oil are obtained, which product is taken up in ethyl ether to give 140 mg of white solid. The filtration liquors are purified by flash chromatography, eluting with 9/1 ethyl acetate/methanol and then 7/3 ethyl acetate/methanol, so as to isolate 40 mg of white solid.

m.p.=207.1-207.6° C.; $[\alpha_D]$=+141° C., c=0.25 wt % MeOH; $^1$H NMR δ (ppm, DMSO-d6): 2.37 (bs, 3H), 2.50-2.74 (m,\*\*), 2.94-3.16 (m, 2H), 7.08 (s, 1H), 7.31 (m, 2H), 7.48 (m, 2H), 7.52 (s, 1H), 8.71 (s, 1H), 10.70 (s, 1H). LCMS: $(M+H)^+$=m/Z 467 amu

EXAMPLE 2

(+)-N-[4,6-Dichloro-3-(4-trifluoromethylphenyl)-2-oxo-2,3-dihydro-1H-indol-3-yl]-2-(1-ethylpiperid-4-yl)acetamide 1) 172.84 mg of $PCl_5$ are added to 4.4 ml of anhydrous dichloromethane cooled in an ice bath, under a stream of nitrogen, followed by slow addition of 142.13 mg of the acid of Preparation 2. The reaction mixture is left to react at 0° C. for 10 minutes and then at room temperature for 3 hours.

2) Separately, 100 mg of the product of Preparation 8 are suspended, under a stream of nitrogen, in 4.4 ml of dichloromethane, followed by addition of 0.1 ml of pyridine. This mixture is cooled in an ice bath. The solution prepared in 1) is added dropwise and stirred at room temperature for one hour. The reaction mixture is poured into water and extracted with ethyl acetate.

The organic phase is washed with saturated $NaHCO_3$ solution, dried over $Na_2SO_4$, filtered and evaporated under vacuum. 145 mg of an orange-coloured solid are obtained, which product is purified on a column by flash chromatography, eluting with 1/1 ethyl acetate/methanol to give 85 mg of product, which is taken up in isopropyl ether to give 75 mg of white/pink solid product.

m.p.=158-162° C.; $[\alpha_D]$=+194°, c=0.125 wt % in MeOH; $^1$H NMR: δ (ppm, DMSO-d6): 0.97 (t, J=7.1 Hz, 3H), 1.07-1.23 (m, 2H), 1.47-1.67 (m, 3H), 1.71-1.85 (m, 2H), 2.07-2.22 (m, 2H), 2.27 (q, J=7.1 Hz, 2H), 2.78 (m, 2H), 6.90 (bs, 1H), 7.18 (bs, 1H), 7.47 (m, 2H), 7.78 (m, 2H), 9.15 (s, 1H), 10.74 (bs, 1H); LCMS: $(M+H)^+$=m/z 514 amu

EXAMPLE 3

N-[4,6-Dichloro-3-(4-chlorophenyl)-2-oxo-2,3-dihydro-1H-indol-3-yl]-2-(4-methylpiperazin-1-yl)acetamide By working as described in Example 2, but using the compound of Preparation 4 instead of the compound of Preparation 2, and the compound of Preparation 7 instead of the compound of Preparation 5, the title compound is obtained.

m.p.=248-251° C.; LC MS: $(M+H)^+$=m/z 467 amu; $^1$H NMR: δ (ppm, DMSO-d6): 2.16 (s, 3H), 2.24-2.42 (m, 4H), 2.43-2.57 (m,\*\*), 2.98-3.12 (m, 2H), 6.92 (d, J=1.8 Hz, 1H), 7.18 (d, J=1.8 Hz, 1H), 7.26 (m, 2H), 7.50 (m, 2H), 8.70 (s, 1H), 10.78 (s, 1H).

EXAMPLE 4

N-[4-Trifluoromethyl-6-cyano-3-(4-chlorophenyl)-2-oxo-2,3-dihydro-1H-indol-3-yl]-2-(4-ethylpiperazin-1-yl)acetamide By working as described in Example 1, but using the product of Preparation 28 instead of the product of Preparation 5, and N-ethylpiperazine instead of N-methylpiperazine, the title compound is obtained.

m.p.=260-262° C.; LCMS: $(M+H)^+$=m/z 506 amu; $^1$H NMR: δ (ppm, DMSO-d6): 0.98 (t, J=7.3 Hz, 3H), 2.23-2.42 (m, 6H), 2.42-2.61 (m, \*\*), 2.87-3.17 (m, 2H), 7.14 (m, 2H), 7.47 (m, 2H), 7.59 (bs, 1H), 7.91 (bs, 1H), 8.91 (s, 1H), 11.12 (bs, 1H).

EXAMPLE 5

(+)-N-[1-Benzoyl-5,6-dichloro-3-(4-chlorophenyl)-2-oxo-2,3-dihydro-1H-indol-3-yl]-2-(4-methylpiperazin-1-yl)acetamide 0.14 g of the compound of Example 1 is placed in 9 ml of DMF in a round-bottomed flask equipped with a magnetic stirrer, and under a stream of nitrogen. 0.01 g of 60% NaH is added, at 0° C. PhCOCl is then added dropwise and the mixture is left to react at room temperature for 2 hours. The reaction mixture is poured into water and extracted with ethyl acetate. The organic phase is dried over $Na_2SO_4$, filtered and evaporated under vacuum. 120 mg of oil are obtained, which product is purified on a column by flash chromatography, eluting with 95/5 ethyl acetate/methanol, to isolate 20 mg of white solid.

m.p.=92-94° C.; $^1$H NMR: δ (ppm, DMSO-d6): 2.16 (s, 3H), 2.24-2.40 (m, 4H), 2.40-2.50 (m, \*\*), 2.94-3.16 (m, 2H), 7.30 (m, 2H), 7.45 (m, 2H), 7.54 (m, 2H), 7.58-7.66 (m, 3H), 7.74 (s, 1H), 8.00 (s, 1H), 9.14 (s, 1H); LCMS: $(M+H)^+$=m/z 571 amu.

EXAMPLE 6

3-(4-Chlorophenyl)-3-[2-(4-ethylpiperazin-1-yl)acetylamino]-2-oxo-4-trifluoromethyl-2,3-dihydro-1H-indole-6-carboxamide 0.16 g of the product obtained in Example 4, 0.47 g of potassium hydroxide and 7 ml of t-BuOH are placed in a round-bottomed flask equipped with a magnetic stirrer. The mixture is left to react at 50° C. for 5 hours. The resulting mixture is filtered through Celite and washed with THF. The filtrate is evaporated under vacuum and the residue is taken up in ethyl acetate and washed with water. The organic phase is dried over $Na_2SO_4$, filtered and evaporated under vacuum. 100 mg of an oil are obtained, which oil is purified by flash chromatography, eluting with 8/2 ethyl acetate/methanol. 10 mg of white solid are isolated.

$^1$H NMR: δ (ppm, DMSO-d6): 0.99 (t, J=7.2 Hz, 3H), 2.25-2.42 (m, 6H), 2.42-2.62 (m, \*\*), 2.92-3.16 (m, 2H), 7.12 (m, 2H), 7.47 (m, 2H), 7.55 (bs, 1H), 7.64 (bs, 1H), 7.84 (bs, 1H), 8.24 (bs, 1H), 8.75 (s, 1H), 10.95 (bs, 1H);

LCMS: $(M+H)^+$=m/z 571 amu.

EXAMPLE 7

N-[6-Chloro-3-(4-chlorophenyl)-1,5-dimethyl-2-oxo-2,3-dihydro-1H-indol-3-yl]-2-(4-methylpiperazin-1-yl)acetamide By working as described in Example 1, but using the product of Preparation 9 instead of the product of Preparation 5, the title compound is obtained.

m.p.=217-219° C.; $^1$H NMR: δ (ppm, DMSO-d6): 2.26-2.35 (m, 6H), 2.44-2.64 (m, **), 2.89-3.15 (m, 5H), 7.19 (s, 1H), 7.25-7.33 (m, 33H), 7.46 (m, 2H), 8.71 (bs, 1H). LCMS: (M+H)$^+$=m/z 461 amu.

EXAMPLE 8

(+)-N-[4,6-Dichloro-3-(4-trifluoromethylphenyl)-2-oxo-2,3-dihydro-1H-indol-3-yl]-2-(1-ethyl-1,2,3,6-tetrahydropyrid-4-yl)acetamide By working as described in Example 2, but using the product of Preparation 10 instead of the product of Preparation 2, the title compound is obtained.

m.p.=155-156° C.; $^1$H NMR: δ (ppm, DMSO-d6): 1.03 (t, J=7.2 Hz, 3H), 2.06 (m, 2H), 2.31-2.65 (m, **), 2.80-3.05 (m, 4H), 5.46 (bs, 1H), 6.91 (d, J=1.7 Hz, 1H), 7.20 (d, J=1.7 Hz, 1H), 7.49 (m, 2H), 7.79 (m, 2H), 9.3 (s, 1H), 10.8 (s, 1H).

LCMS: (M+H)$^+$=m/z 459 amu

Table 2 below illustrates the chemical structures and the physical properties of a few examples of compounds according to the invention. In this table:

- in the "stereoisomer" column, "rac" represents a racemic mixture, and (+) or (−) represents one or other of the stereoisomers,
- in the "salt" column, "-" represents a compound in free base form, whereas "HCl" represents a compound in hydrochloride form and the ratio in parentheses is the (acid:base) ratio,
- Me, Et, n-Pr, i-Pr, n-Bu and i-Bu represent, respectively, methyl, ethyl, n-propyl, isopropyl, n-butyl and isobutyl groups, and
- Ph and Bn represents, respectively, phenyl and benzyl groups.

TABLE 2

| Ex. No. | —X⟨ | Y | Ar | R$_1$ | R$_2$ | R$_3$ | R$_4$ | R$_5$ | n | Salt | Isomer | αD, LCMS or m.p. |
|---|---|---|---|---|---|---|---|---|---|---|---|---|
| 1 | —N< | >N— | 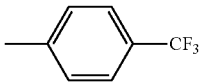 4-Cl-phenyl | H | 6-Cl | 5-Cl | H | Me | 1 | — | (+) | 167-168° C. |
| 2 | —CH< | >N— | 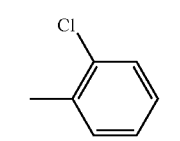 4-CF$_3$-phenyl | H | 6-Cl | H | 4-Cl | Et | 1 | — | (+) | 158-162° C. |
| 3 | —N< | >N— | 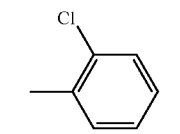 2-Cl-phenyl | H | 6-Cl | 5-Me | H | Me | 1 | — | rac | 256-258° C. |
| 4 | —N< | >N— | 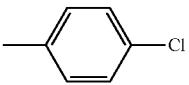 2-Cl-phenyl | H | 6-Cl | 5-Me | H | Me | 2 | — | rac | 130° C. |
| 5 | —N< | >N— | 4-Cl-phenyl | H | 6-Cl | 5-Me | H | Me | 1 | — | rac | m/z = 447 |

TABLE 2-continued

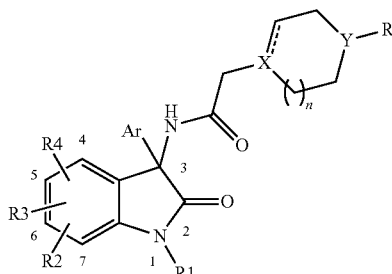

| Ex. No. | X | Y | Ar | R₁ | R₂ | R₃ | R₄ | R₅ | n | Salt | Isomer | αD, LCMS or m.p. |
|---|---|---|---|---|---|---|---|---|---|---|---|---|
| 6 | —N< | >N— | 3-Cl-phenyl | H | 6-Cl | 5-Me | H | Me | 1 | — | rac | m/z = 447 |
| 7 | —N< | >N— | 4-OMe-phenyl | H | 6-Cl | 5-Cl | H | Me | 1 | — | rac | 263° C. |
| 8 | =C(CH₃)– | >N— | 4-CF₃-phenyl | H | 6-Cl | H | 4-Cl | Et | — | — | (+) | m/z = 512 |
| 9 | —N< | >N— | 2,4-diCl-phenyl | H | 6-Cl | 5-Me | H | Me | 1 | — | rac | 144° C. |
| 10 | —N< | >N— | 4-Cl-phenyl | H | 6-Cl | 5-Me | H | Me | 1 | — | (+) | 152-153° C. |
| 11 | —N< | >N— | 4-Cl-phenyl | H | 6-Cl | 5-Me | H | Me | 1 | — | (−) | 185° C. |
| 12 | —N< | >N— | 4-OMe-phenyl | H | 6-Cl | 5-Me | H | Me | 1 | — | rac | 256° C. |
| 13 | —N< | >N— | 3,4-diCl-phenyl | H | H | 5-Me | 4-Cl | Me | 1 | — | rac | 282-284° C. |
| 14 | —N< | >N— | 4-Cl-phenyl | H | 6-Cl | 5-Me | H | Me | 1 | — | rac | 229-232° C. |
| 15 | —N< | >N— | 4-Cl-phenyl | H | 6-Me | 5-Cl | H | Me | 1 | — | rac | 267-269° C. |
| 16 | —N< | >N— | 4-Cl-phenyl | H | 6-Cl | 5-Me | H | Et | 1 | — | rac | 223-224° C. |

TABLE 2-continued
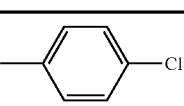
| Ex. No. | X | Y | Ar | R1 | R2 | R3 | R4 | R5 | n | Salt | Isomer | αD, LCMS or m.p. |
|---|---|---|---|---|---|---|---|---|---|---|---|---|
| 17 | —N< | >N— | 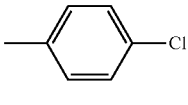 | H | 6-Cl | 5-Cl | H | Me | 2 | — | rac | 214-216° C. |
| 18 | —N< | >N— | 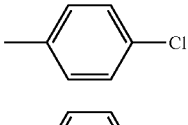 | H | 6-Cl | 5-Cl | H | Me | 1 | — | (−) | 188-190° C. |
| 19 | —N< | >N— | 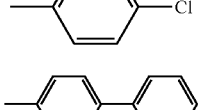 | H | 6-Cl | 5-Cl | 4-Cl | Me | 1 | — | rac | 276-278° C. |
| 20 | —N< | >N— | 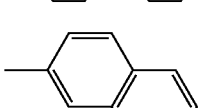 | H | 6-I | H | 4-CF$_3$ | Me | 1 | — | rac | 231-232° C. |
| 21 | —N< | >N— | 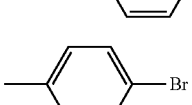 | H | 6-Cl | 5-Cl | H | Me | 1 | — | rac | 181-182° C. |
| 22 | —N< | >N— | 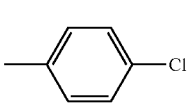 | H | 6-Cl | 5-Cl | H | Me | 1 | — | rac | 237-238° C. |
| 23 | —N< | >N— | 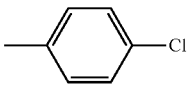 | H | 6-Cl | 5-Cl | H | Me | 1 | — | rac | 291-294° C. |
| 24 | —N< | >N— | 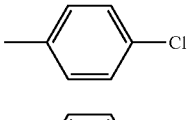 | H | 6-Cl | 5-Cl | H | Me | 1 | — | rac | 293-294° C. |
| 25 | —N< | >N— | 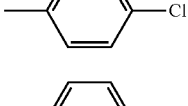 | H | 6-Cl | 5-Cl | H | Et | 1 | — | rac | 227-229° C. |
| 26 | —N< | >CH— | 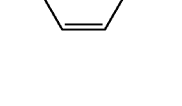 | H | 6-Cl | 5-Cl | H | Me | 1 | — | rac | 261-262° C. |
| 27 | —N< | >N— |  | H | 6-Cl | H | 4-Cl | Me | 1 | — | rac | 248-251° C. |
| 28 | —N< | >N— |  | H | 7-Cl | 5-Cl | H | Me | 1 | — | rac | 260-261° C. |

TABLE 2-continued
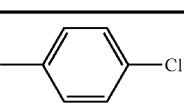
| Ex. No. | X | Y | Ar | R1 | R2 | R3 | R4 | R5 | n | Salt | Isomer | αD, LCMS or m.p. |
|---|---|---|---|---|---|---|---|---|---|---|---|---|
| 29 | —N< | >N— | 4-Cl-C6H4 | H | 6-Cl | 5-Cl | H | Et | 2 | — | rac | 189-190° C. |
| 30 | —N< | >N— | 4-CF3-C6H4 | H | 6-Cl | 5-Cl | H | Me | 1 | — | rac | 267-269° C. |
| 31 | —N< | >N— | 4-C(CH3)3-C6H4 | H | 6-Cl | 5-Cl | H | Me | 1 | — | rac | 207-209° C. |
| 32 | —N< | >N— | 4-Cl-C6H4 | H | 6-Cl | 5-Me | H | Et | 1 | — | (+) | 158-159° C. |
| 33 | —N< | >N— | 4-Cl-C6H4 | H | 6-Cl | 5-Cl | H | Et | 1 | — | (+) | 160-163° C. |
| 34 | —N< | >N— | 4-F-C6H4 | H | 6-Cl | 5-Cl | H | Me | 1 | — | rac | 282-284° C. |
| 35 | —N< | >N— | 4-F-C6H4 | H | 6-Cl | 5-Cl | H | Et | 1 | — | rac | 274-275° C. |
| 36 | —N< | >N— | 4-Cl-C6H4 | H | 6-Cl | H | 4-Cl | Me | 1 | — | (+) | 157-158° C. |
| 37 | —N< | >N— | 4-Cl-C6H4 | H | 6-Cl | H | 4-Cl | Et | 1 | — | (+) | 155° C. |
| 38 | —N< | >N— | 4-CF3-C6H4 | H | 6-Cl | 5-Cl | H | Me | 1 | — | (+) | 255-256° C. |
| 39 | —N< | >N— | 4-CF3-C6H4 | H | 6-Cl | 5-Cl | H | CH(Me)2 | 1 | — | (+) | 221° C. |
| 40 | —N< | >N— | 4-Br-C6H4 | H | 6-Cl | 5-Cl | H | Me | 1 | — | (+) | 292-294° C. |

TABLE 2-continued

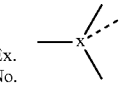

| Ex. No. | X | Y | Ar | R₁ | R₂ | R₃ | R₄ | R₅ | n | Salt | Isomer | αD, LCMS or m.p. |
|---|---|---|---|---|---|---|---|---|---|---|---|---|
| 41 | —N< | >N— | 4-Br-phenyl | H | 6-Cl | 5-Cl | H | Et | 1 | — | (+) | 198-201° C. |
| 42 | —N< | >N— | 4-Cl-phenyl | H | 6-Cl | 5-Cl | H | Me | 2 | — | (+) | 214-216° C. |
| 43 | —N< | >N— | 4-Cl-phenyl | —C(O)—Ph | 6-Cl | 5-Cl | H | Me | 1 | — | (+) | 92-94° C. |
| 44 | —N< | >N— | 4-Cl-phenyl | —C(O)—Ph | 6-Cl | 5-Cl | H | Me | 1 | — | rac | 198° C. |
| 45 | —N< | >N— | 4-Cl-phenyl | —C(O)—CH₃ | 6-Cl | 5-Cl | H | Me | 1 | — | rac | 225° C. |
| 46 | —N< | >N— | 4-Cl-phenyl | —Me | 6-Cl | 5-Me | H | Me | 1 | — | rac | 217-219° C. |
| 47 | —N< | >N— | 4-Cl-phenyl | —C(O)—CH₃ | 6-Cl | 5-Cl | H | Et | 1 | — | rac | 93-94° C. |
| 48 | —N< | >N— | 4-Cl-phenyl | —C(O)—Ph | 6-Cl | 5-Cl | H | Et | 1 | — | rac | 194-195° C. |
| 49 | —N< | >N— | 4-Br-phenyl | —C(O)—CH₃ | 6-Cl | 5-Cl | H | Me | 1 | — | rac | 223-224° C. |
| 50 | —N< | >N— | 4-Cl-phenyl | H | 6-Cl | 5-Cl | H | Me | 1 | — | rac | 293-294° C. |
| 51 | —CH< | >N— | 5-Cl-2-methylthiophene | H | 4-Cl | 6-Cl | H | Et | 1 | — | (+) | m/z = 486 |
| 52 | —N< | >N— | 4-Br-phenyl | H | 4-Cl | 6-CF3 | H | Et | 1 | — | (+) | m/z = 558 |

TABLE 2-continued

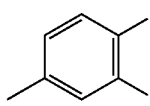

| Ex. No. | X | Y | Ar | R₁ | R₂ | R₃ | R₄ | R₅ | n | Salt | Isomer | αD, LCMS or m.p. |
|---|---|---|---|---|---|---|---|---|---|---|---|---|
| 53 | —N< | >N— | 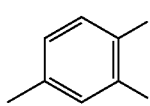 2,3-diCl-phenyl | H | 4-Cl | 6-Cl | H | Et | 1 | — | (+) | m/z = 515 |
| 54 | —CH< | >N— | 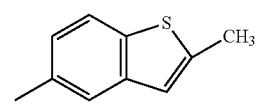 2,3-diCl-phenyl | H | 4-Cl | 6-Cl | H | Et | 1 | — | (+) | 211-213° C. |
| 55 | —CH< | >N— | 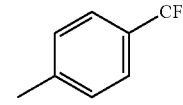 2-Me-benzothiophene | H | 4-Cl | 6-Cl | H | Et | 1 | — | (+) | m/z = 516 |
| 56 | —CH< | >N— |  4-CF₃-phenyl | —C(=O)CH₃ | 4-Cl | 6-Cl | H | Et | 1 | — | (+) | 162-163° C. |
| 57 | —CH< | >N— | 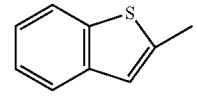 2-Me-benzothiophene | H | 4-Cl | 6-Cl | H | Et | 1 | — | (+) | m/z = 502 |
| 58 | —CH< | >N— | 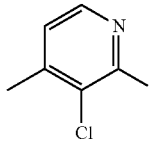 2,3-diCl-pyridyl | H | 4-Cl | 6-Cl | H | Et | 1 | — | (+) | 177° C. |
| 59 | —CH< | >N— | 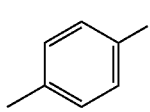 4-Cl-phenyl | —Me | 4-Cl | 6-Cl | H | Et | 1 | — | rac | 293° C. |
| 60 | —CH< | >N— | 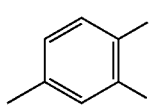 4-Cl-3-F-phenyl | H | 4-Cl | 6-Cl | H | Et | 1 | — | (+) | 196-200° C. |
| 61 | —N< | >N— | 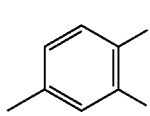 4-Cl-3-F-phenyl | H | 4-Cl | 6-Cl | H | Et | 1 | — | (+) | m/z = 499 |
| 62 | —N< | >N— | 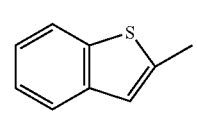 2-Me-benzothiophene | H | 4-Cl | 6-Cl | H | Et | 1 | — | (+) | m/z = 503 |

TABLE 2-continued
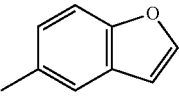
| Ex. No. | X | Y | Ar | R₁ | R₂ | R₃ | R₄ | R₅ | n | Salt | Isomer | αD, LCMS or m.p. |
|---|---|---|---|---|---|---|---|---|---|---|---|---|
| 63 | —CH< | >N— | 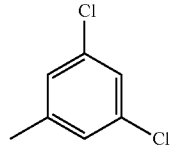 | H | 4-Cl | 6-Cl | H | Et | 1 | — | (+) | 163-166° C. |
| 64 | —N< | >N— | 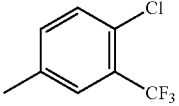 | H | 4-Cl | 6-Cl | H | Et | 1 | — | (+) | 140-142° C. |
| 65 | —N< | >N— | 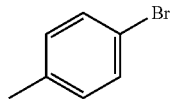 | H | 4-Cl | 6-Cl | H | Et | 1 | HCl | (+) | 150-156° C. |
| 66 | —N< | >N— | 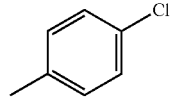 | H | 4-CF3 | 6-OMe | H | Et | 1 | — | (+) | m/z = 555 |
| 67 | —CH< | >N— | 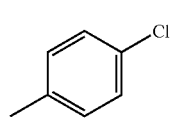 | —Me | 4-Cl | 6-Cl | H | Et | 1 | — | (−) | αD = −205°, c = 0.135 in MeOH |
| 68 | —CH< | >N— | 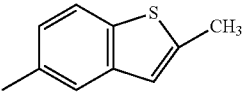 | —Me | 4-Cl | 6-Cl | H | Et | 1 | — | (+) | αD = +145°, c = 0.28 in MeOH |
| 69 | —N< | >N— | 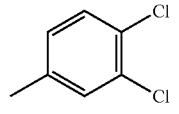 | H | 4-Cl | 6-Cl | H | Et | 1 | — | (+) | 180-182° C. |
| 70 | —N< | >N— | 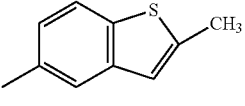 | H | 4-Cl | 6-Cl | 5-F | Et | 1 | — | (+) | 148-150° C. |
| 71 | —CH< | >N— | 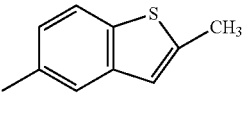 | i-Pr | 4-Cl | 6-Cl | H | Et | 1 | — | rac. | 163-165° C. |
| 72 | —CH< | >N— |  | Et | 4-Cl | 6-Cl | H | Et | 1 | — | rac. | 154-156° C. |

TABLE 2-continued

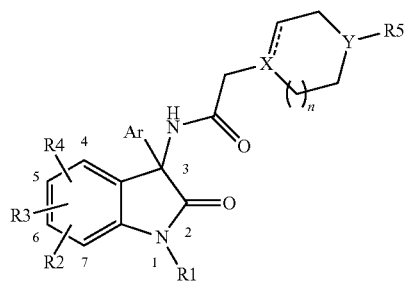

| Ex. No. | X | Y | Ar | R₁ | R₂ | R₃ | R₄ | R₅ | n | Salt | Isomer | αD, LCMS or m.p. |
|---|---|---|---|---|---|---|---|---|---|---|---|---|
| 73 | —N< | >N— | 2,3-diCl-phenyl | H | 4-Cl | 6-Cl | H | allyl (CH₂CH=CH₂) | 1 | — | (+) | m/z = 527 |
| 74 | —CH< | >N— | 2,3-diCl-phenyl | i-Pr | 4-Cl | 6-Cl | H | Et | 1 | — | (+) | 115-116° C. |
| 75 | —N< | >N— | 2-methylbenzofuran-5-yl | H | 4-Cl | 6-Cl | H | Et | 1 | — | (+) | 140-142° C. |
| 76 | —CH< | >N— | 2,3-diCl-phenyl | Et | 4-Cl | 6-Cl | H | Et | 1 | HCl | (−) | 218-220° C. |
| 77 | —CH< | >N— | 2-methylbenzothiophen-5-yl | i-Pr | 4-Cl | 6-Cl | H | Et | 1 | — | (+) | αD = −244°, c = 0.11 in MeOH |
| 78 | —CH< | >N— | 2-methylbenzothiophen-5-yl | i-Pr | 4-Cl | 6-Cl | H | Et | 1 | — | (−) | αD = −226°, c = 0.10 in MeOH |
| 79 | —CH< | >N— | 2-methylbenzothiophen-5-yl | Et | 4-Cl | 6-Cl | H | Et | 1 | — | (+) | αD = +242°, c = 0.11 in MeOH |
| 80 | —CH< | >N— | 2-methylbenzothiophen-5-yl | Et | 4-Cl | 6-Cl | H | Et | 1 | — | (−) | αD = −250°, c = 0.10 in MeOH |
| 81 | —N< | >N— | 2-methylbenzothiazol-5-yl | H | 4-Cl | 6-Cl | H | Et | 1 | — | (+) | 147-148° C. |

TABLE 2-continued
| Ex. No. | X | Y | Ar | R1 | R2 | R3 | R4 | R5 | n | Salt | Isomer | αD, LCMS or m.p. |
|---|---|---|---|---|---|---|---|---|---|---|---|---|
| 82 | —N< | >N— | 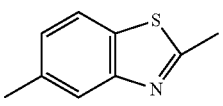 | H | 4-Cl | 6-Cl | H | Et | 1 | — | (−) | m/z = 504 |
| 83 | —N< | >N— | 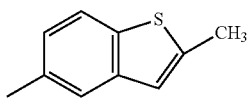 | H | 4-Cl | 6-Cl | H | Me | 1 | — | (+) | m/z = 503 |
| 84 | —N< | >N— | 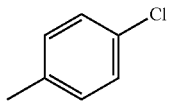 | H | H | 6-Br | H | Et | 1 | — | (+) | 176-178° C. |
| 85 | —N< | >N— | 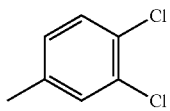 | H | 4-Cl | 6-Cl | H | Me | 2 | Oxalate | (+) | 176-180° C. |
| 86 | —N< | >N— | 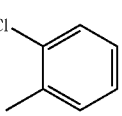 | —C(O)—CH3 | 5-Me | 6-Cl | H | Et | 1 | Oxalate | (+) | 137-141° C. |
| 87 | —N< | >N— |  | H | 4-Cl | 6-Cl | H | Me | 1 | Oxalate | (+) | 202-204° C. |
| 88 | —N< | >N— | 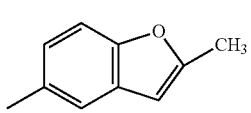 | H | H | 6-Br | H | Me | 1 | — | (+) | 186-187° C. |
| 89 | —N< | >N— | 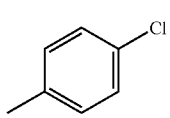 | H | H | 6-Cl | H | Et | 1 | — | (+) | 168° C. |
| 90 | —N< | >N— | 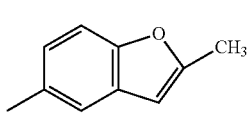 | H | H | 6-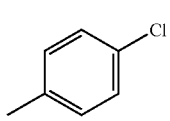 | H | Et | 1 | — | (+) | 350° C. |
| 91 | —N< | >N— |  | H | 4-Cl | 6-Cl | H | Et | 1 | — | (+) | 135-137° C. |

TABLE 2-continued

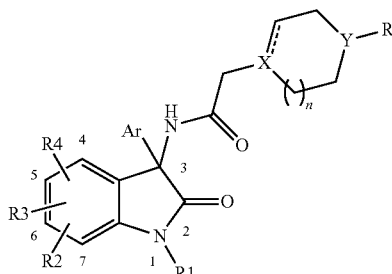

| Ex. No. | X | Y | Ar | R₁ | R₂ | R₃ | R₄ | R₅ | n | Salt | Isomer | αD, LCMS or m.p. |
|---|---|---|---|---|---|---|---|---|---|---|---|---|
| 92 | —N< | >N— | 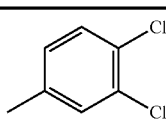 2,4-diCl-phenyl | H | H | 6-Cl | H | Et | 1 | — | (+) | 197° C. |
| 93 | —N< | >N— | 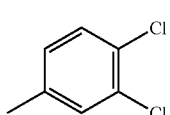 2,4-diCl-phenyl | H | H | 6-Cl | H | Me | 1 | — | (+) | 176° C. |
| 94 | —N< | >N— | 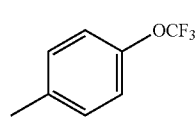 4-OCF₃-phenyl | H | H | 6-Br | H | Et | 1 | Oxalate | (+) | 161° C. |
| 95 | —N< | >N— | 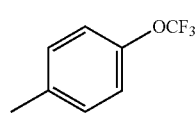 4-OCF₃-phenyl | H | H | 6-Cl | H | Et | 1 | — | (+) | m/z = 497 |
| 96 | —N< | >N— | 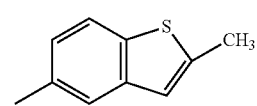 2-methylbenzothiophene | H | 4-Cl | 6-Cl | H | Me | 2 | Oxalate | rac | 205° C. |
| 97 | —N< | >N— | 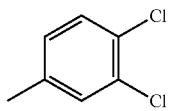 3,4-diCl-phenyl | H | H | 6-Br | H | Et | 1 | Oxalate | (+) | 190° C. |
| 98 | —N< | >N— | 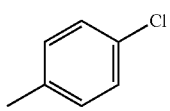 4-Cl-phenyl | H | H | 5-Br | H | Et | 1 | — | (+) | 123° C. |
| 99 | —N< | >N— | 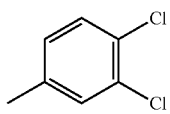 3,4-diCl-phenyl | H | H | 6-Br | H | Me | 1 | Oxalate | (+) | 188° C. |
| 100 | —N< | >N— | 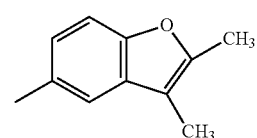 2,3-dimethylbenzofuran | H | 4-Cl | 6-Cl | H | Et | 1 | — | (+) | 195° C. |
| 101 | —N< | >N— | 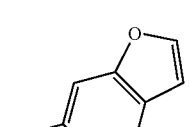 benzofuran | H | 4-Cl | 6-Cl | H | Et | 1 | Oxalate | (+) | 167° C. |

TABLE 2-continued

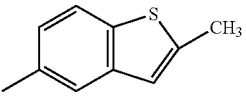

| Ex. No. | —X | Y | Ar | R$_1$ | R$_2$ | R$_3$ | R$_4$ | R$_5$ | n | Salt | Iso-mer | αD, LCMS or m.p. |
|---|---|---|---|---|---|---|---|---|---|---|---|---|
| 102 | —N< | >N— | 5-methyl-2-methylbenzothiophene | H | H | 6-Br | H | Et | 1 | Oxa-late | (+) | 189° C. |
| 103 | —N< | >N— | 5-methyl-2-methylbenzothiophene | H | H | 6-Cl | H | Et | 1 | — | (+) | m/z = 483 |
| 104 | —N< | >N— | 6-methyl-3-methylpyridine | H | H | 6-Cl | H | Et | 1 | Oxa-late | rac | m/z = 428 |

EXAMPLE 53

$^1$H NMR: δ (ppm, DMSO-d6): 0.86-1.15 (m; 3H); 2.52-2.78 (m; **); 3.02-3.19 (m; *); 6.93 (d; J=1.5 Hz; 1H); 7.06 (dd; Ja=8 Hz; Jb=2 Hz; 1H); 7.21 (d; J=1.5 Hz; 1H); 7.56 (d; J=2 Hz; 1H); 7.67 (d; J=8 Hz; 1H); 8.96 (bs; 1H); 10.88 (s; 1H).

EXAMPLE 61

$^1$H NMR: δ (ppm, DMSO-d6): 1.08-1.37 (m; 3H); 2.55-3.50 (m; **; *); 6.94 (d; J=2 Hz; 1H); 6.98 (dd; Ja=8 Hz; Jb=2 Hz; 1H); 7.21 (d; J=2 Hz; 1H); 7.33 (dd; Ja=10 Hz; Jb=2 Hz; 1H); 7.63 (m; 1H); 8.99 (s; 1H); 9.83 (bs; 1H); 10.88 (s; 1H).

EXAMPLE 65

$^1$H NMR: δ (ppm, DMSO-d6): 1.14-1.28 (m; 3H); 2.55-2.80 (m; 2H); 2.80-3.74 (m; *); 6.96 (d; J=2 Hz; 1H); 7.24 (d; J=2 Hz; 1H); 7.36 (dd; Ja=8 Hz; Jb=2 Hz; 1H); 7.75 (d; J=8 Hz; 1H); 7.84 (d; J=2 Hz; 1H); 9.27 (s; 1H); 9.90 (bs; 1H); 10.96 (s; 1H).

EXAMPLE 72

$^1$H NMR: δ (ppm, DMSO-d6): 0.96-1.14 (m; 6H); 1.14-1.46 (m; 4H); 1.49-1.63 (m; 1H); 1.63-1.83 (m; 2H); 2.16 (dd; Ja=13 Hz; Jb=7 Hz; 1H); 2.23 (dd; Ja=13 Hz; Jb=7 Hz; 1H); 2.55 (s; 3H); 2.81-3.12 (m; 2H); 3.65 (m→q; J=7 Hz; 2H); 7.08-7.19 (m; 2H); 7.22 (d; J=1.8 Hz; 1H); 7.30 (d; J=1.8 Hz; 1H); 7.57 (d; J=2 Hz; 1H); 7.86 (d; J=9 Hz; 1H); 9.16 (bs; 1H).

EXAMPLE 75

$^1$H NMR: δ (ppm, DMSO-d6): 0.98 (t; J=7 Hz; 3H); 2.29 (m→q; J=7 Hz; 2H); 2.33-2.41 (m; 4H); 2.44 (s; 3H); 2.52-2.63 (m; **); 3.01 (d; J=15 Hz; 1H); 3.07 (d; J=15 Hz; 1H); 6.61 (s; 1H); 6.91 (d; J=2 Hz; 1H); 7.11 (dd; Ja=8 Hz; Jb=2 Hz; 1H); 7.18 (d; J=2 Hz; 1H); 7.37 (d; J=2 Hz; 1H); 7.52 (d; J=8 Hz; 1H); 8.60 (s; 1H); 10.69 (bs; 1H).

EXAMPLE 79

$^1$H NMR: δ (ppm, DMSO-d6): 0.98 (t; J=7 Hz; 3H); 2.30 (m→q; J=7 Hz; 2H); 2.33-2.58 (m; **); 3.02 (d; J=15 Hz; 1H); 3.08 (d; J=15 Hz; 1H); 6.92 (d; J=1.6 Hz; 1H); 7.20 (d; J=1.6 Hz; 1H); 7.33-7.41 (m; 2H); 7.41-7.47 (m; 2H); 8.78 (bs; 1H); 10.79 (bs; 1H).

EXAMPLE 91

$^1$H NMR: δ (ppm, DMSO-d6): 0.99 (t; J=7 Hz; 3H); 1.07 (t; J=7 Hz; 3H); 1.12-1.29 (m; 2H); 1.47-1.57 (m; 1H); 1.57-1.72 (m; 2H); 1.81-1.98 (m; 2H); 2.12 (dd; Ja=13 Hz; Jb=7 Hz; 1H); 2.22 (dd; Ja=13 Hz; Jb=7 Hz; 1H); 2.26-2.40 (m; 2H); 2.55 (s; 3H); 2.76-2.91 (m; 2H); 3.64 (m→q; J=7 Hz; 2H); 7.07-7.18 (m; 2H); 7.22 (bs; 1H); 7.29 (bs; 1H); 7.57 (bs; 1H); 7.83 (d; J=9 Hz; 1H); 9.13 (bs; 1H).

The compounds according to the invention underwent in vivo studies.

In Vivo Test

Male Crl CD BR rats (Charles River, Italy) weighing 150-175 g were housed in a chamber at regulated temperature (22±1° C.) and humidity (55±10%) and with a 12-hour lightness-darkness cycle, for at least 7 days before their use. Feed and water were available ad libitum. The feed was removed 18 hours before sacrificing the animals. The rats were sacrificed by cervical dislocation, and the stomach was removed surgically, opened along the shorter curvature and placed in a Krebs solution (of composition (mM): 118.4 NaCl; 4.7 KCl;

2.5 CaCl$_2$; 3.7 NaH$_2$PO$_4$; 1.2 MgSO$_4$; 25 NaHCO$_3$; 5.6 glucose). The animals were cared for and sacrificed according to the Sanofi-Aventis international code of ethics and the international principles governing the care and treatment of laboratory animals (EEC Directive 86/609, DJL358, 1, 12 Dec. 1987). Strips of approximately 1 cm (5 mm wide) of gastric fundus were cut out along the longitudinal axis and suspended in 20 ml of bath filled with the Krebs solution at 37° C. and aerated with a 95% O$_2$-5% CO$_2$ gas mixture. The strips were maintained at a resting load of 1 g and, after washing, 10 µM of choline (acetylcholine precursor) and 10 µM of indomethacin (prostaglandin synthetase inhibitor) were added to the medium, to reduce the spontaneous phasic contractions (Depoortere et al., *Eur. J. Pharmacol.* 515, 1-3, 160-168, 2003; Dass et al., *Neurosciences* 120, 443-453, 2003). Isotonic contractions were initiated by stimulation with an electric field. Two platinum wire electrodes were placed at the surface and at the bottom of the organ bath, and the electric-field stimulation was performed with a Power Lab stimulator (AD Instruments Pty Ltd, Castle Hill, Australia) coupled to a multiplex pulse propeller (Ugo Basile, Varese, Italy) (Fukuda et al., *Scand. J. Gastroenterol.* 12, 1209-1214, 2004). The supramaximal stimulation was applied to create maximum contractions (20 Hz, pulse width: 2 milliseconds; 5 volts; batch trains every 2 minutes, 150 mA). Next, the current was reduced to obtain a submaximal stimulation (50% reduction of the maximum contractile response). The contractions were recorded by computer with a data recording and analysis system (Power Lab, Chart 5) connected to isotonic transducers (Ugo Basile, Varese, Italy) via preamplifiers (Octal Bridge Amp). After stabilization, concentration-response cumulative curves for ghrelin (0.1 nM-1 µM) were plotted, with and without incubation (contact time: 30 minutes) of the antagonist molecules. Supramaximal electric-field stimulation was used for each strip as reference (100%) to classify the responses per test substance. The agonist concentration producing 50% of the maximum effect ($EC_{50}$) was calculated using a four-parameter logistic model according to Ratkovsky and Reedy (*Biometrics*, 42, 575-582, 1986), with adjustment by non-linear regression using the Levenberg-Marquard algorithm in the Everstat software. The pKb values for the antagonists were calculated according to the Cheng-Prusoff equation (Kenakin et al., Competitive Antagonism, *Pharmacologic Analysis of Drug-Receptor Interaction,* 3rd edition, 331-373, Philadelphia, New York; Raven: Lippincott, 1997).

The compounds of formula (I) show antagonist activity towards the ghrelin receptor with $IC_{50}$ values ranging from $10^{-6}$ to $10^{-11}$ M.

For example, compounds 1 and 2 have an $IC_{50}$ value of $5 \times 10^{-8}$ M and $1 \times 10^{-9}$ M, respectively.

It is thus seen that the compounds according to the invention have antagonist activity towards the ghrelin receptor.

The compounds according to the invention may thus be used for the preparation of medicaments, in particular medicaments for preventing or treating any pathology in which the ghrelin receptor is involved.

Thus, according to another of its aspects, a subject of the invention is medicaments comprising a compound of formula (I) or an addition salt thereof with a pharmaceutically acceptable acid.

Thus, the compounds according to the invention may be used, for man and animals, in the treatment or prevention of various ghrelin-dependent complaints. Thus, the compounds according to the invention may be used as anorexic agents, for regulating the appetite, the taking of meals and their frequency, and also, in the long-term, the weight, especially weight gain following diets or therapeutic regimens. The compounds according to the invention are thus particularly useful for preventing or treating obesity, appetite disorders, diabetes, excess weight and/or the effects thereof.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt thereof, and also at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the salt thereof, may be administered in unit administration form, as a mixture with standard pharmaceutical excipients, to animals and human beings, for the prophylaxis or treatment of the above disorders or diseases.

The appropriate unit administration forms include oral-route forms such as tablets, soft or hard gel capsules, powders, granules and oral solutions or suspensions, sublingual, buccal, intratracheal, intraocular or intranasal administration forms, forms for administration by inhalation, topical, transdermal, subcutaneous, intramuscular or intravenous administration forms, rectal administration forms and implants. For topical application, the compounds according to the invention may be used in creams, gels, ointments or lotions.

By way for example, a unit administration form of a compound according to the invention in tablet form may comprise the following components:

| | |
|---|---:|
| Compound according to the invention | 50.0 mg |
| Mannitol | 223.75 mg |
| Sodium crosscarmellose | 6.0 mg |
| Corn starch | 15.0 mg |
| Hydroxypropylmethylcellulose | 2.25 mg |
| Magnesium stearate | 3.0 mg |

Via the oral route, the dose of active principle administered per day may be from 0.1 to 100 mg/kg in one or more dosage intakes. Via the parenteral route, it may be from 0.01 to 10 mg/kg/day There may be particular cases in which higher or lower dosages are appropriate; such dosages do not depart from the scope of the invention. According to the usual practice, the dosage that is appropriate to each patient is determined by the practitioner according to the mode of administration, and the weight and response of the said patient.

Possible Combinations

The present invention also relates to combinations of one or more compound(s) according to the invention of general formula (I) with one or more active ingredient(s).

As active ingredient(s) that is (are) suitable for the said combinations, mention may be made especially of anti-obesity and antidiabetic agents, and also rimonabant, metformin or sulfonylureas.

According to another of its aspects, the present invention also relates to a method for treating the pathologies indicated above, which comprises the administration to a patient of an effective dose of a compound according to the invention, or of a pharmaceutically acceptable salt thereof.

According to another of its aspects, the present invention also relates to a compound of formula (I), or a pharmaceutically acceptable salt thereof, for treating the pathologies indicated above.

The invention claimed is:
1. A compound corresponding to formula (I):

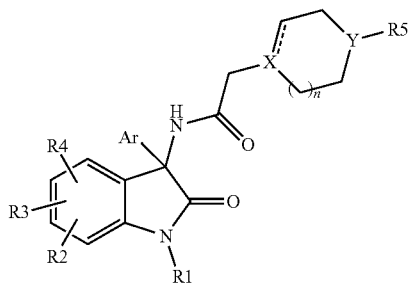

in which:
= represents a single or double bond,
X represents —N<, —CH< or

Y represents >N— or >CH—, wherein at least one from among X and Y represents N;
Ar represents an aryl or heteroaryl group optionally substituted with one or more substituents, which may be identical or different, chosen from halogen atoms and (C1-6)alkyl, (C1-6)haloalkyl, perhalo(C1-3)alkyl, (C1-6)alkoxy, perhalo(C1-3)alkoxy and aryl groups;
R1 represents a hydrogen atom or a (C1-6)alkyl, —C(=O)(C1-6)alkyl or —C(=O)aryl group;
R2, R3 and R4, which may be identical or different, located on any of the available positions of the phenyl nucleus, independently represent a hydrogen atom, a halogen atom, CN, OH, a (C1-6)alkyl group optionally substituted with a halogen atom or an OH; perhalo(C1-3)alkyl, (C1-6)alkoxy, perhalo(C1-3)alkoxy, aminocarbonyl, (C1-6)alkylaminocarbonyl, di(C1-6)alkylaminocarbonyl, aryl, aryloxy; heteroaryl; the aryl, aryloxy or heteroaryl group being optionally substituted with a halogen atom, CN, OH or a (C1-6)alkyl, perhalo(C1-3)alkyl or (C1-6)alkoxy group; whereby at least one from among R2, R3 and R4 is other than H;
R5 represents a (C1-6)alkyl or (C2-6)alkenyl group; and
n represents 1 or 2;
in the form of the base or of an acid-addition salt; with the exclusion of 5-chloro-3-(2-chlorophenyl)-1,3-dihydro-3-[2-(4-methylpiperazin-1-yl)acetamido]indol-2-one.
2. The compound of claim 1 wherein:
= represents a single or double bond;
X represents —CH<, —N< or

Y represents >N— or >CH—, wherein at least one from among X and Y represents N;
Ar represents an aryl or heteroaryl group optionally substituted with one or more substituents, which may be identical or different, chosen from halogen atoms and (C1-6)alkyl, perhalo(C1-3)alkyl, (C1-6)alkoxy and aryl groups;
R1 represents a hydrogen atom or a —C(=O)(C1-6)alkyl, —C(=O)aryl or (C1-6)alkyl group;
R2, R3 and R4, which may be identical or different, located on any of the available positions of the phenyl nucleus, independently represent a hydrogen atom, a halogen atom, a (C1-6)alkyl, perhalo(C1-3)alkyl, CN, aryl, heteroaryl, OH, (C1-6)alkoxy, perhalo(C1-3)alkoxy, aminocarbonyl, (C1-6) (C1-6)alkylaminocarbonyl or di(C1-6)alkylaminocarbonyl group, whereby at least one from among R2, R3 and R4 is other than H;
R5 represents a (C1-6)alkyl group;
n represents 1 or 2;
in the form of the base or of an acid-addition salt.
3. The compound according to claim 2 wherein Ar is an aryl group substituted by Cl or Br.
4. The compound of claim 2 wherein:
= represents a single or double bond;
X represents —N<, —CH< or

Y represents >N— or >CH—;
wherein at least one from among X and Y represents N;
Ar represents an aryl group optionally substituted with one or more substituents chosen from halogen, (C1-6)alkoxy, (C1-6)alkyl, aryl, trifluoromethyl and trifluoromethoxy groups;
R1 represents a hydrogen atom or a —C(=O)(C1-6)alkyl, —C(=O)aryl or (C1-6)alkyl group;
R2, R3 and R4, which may be identical or different, located on any of the available positions of the phenyl nucleus, independently represent a hydrogen atom, a halogen atom, or a (C1-6)alkyl or trifluoromethyl group, whereby at least one from among R2, R3 and R4 is other than H;
R5 represents a (C1-6)alkyl group;
n represents 1 or 2;
in the form of the base or of an acid-addition salt.
5. The compound of claim 4 wherein halogen in R2, R3 and R4 is chlorine or bromine.
6. The compound of claim 4 wherein:
= represents a single or double bond;
X represents —N<, —CH< or

Y represents >N— or >CH—; wherein at least one from among X and Y represents N;
Ar represents a phenyl or naphthyl group optionally substituted with one or more substituents chosen from halogen atoms, preferentially chlorine or bromine, and methoxy, methyl, tert-butyl, phenyl, trifluoromethyl and trifluoromethoxy groups;

R1 represents a hydrogen atom or a —C(=O)methyl, —C(=O)phenyl or methyl group;

R2, R3 and R4, which may be identical or different, located on any of the available positions of the phenyl nucleus, independently represent a hydrogen atom, a halogen atom or trifluoromethyl group, whereby at least one from among R2, R3 and R4 is other than H;

R5 represents a methyl, ethyl or 2-propyl group;

n represents 1 or 2;

in the form of the base or of an acid-addition salt.

7. The compound of claim 2 wherein:

Ar represents a heteroaryl group optionally substituted with one or more substituents, which may be identical or different, chosen from halogen atoms and (C1-6)alkoxy, aryl, perhalo(C1-3)alkyl and (C1-6)alkyl groups.

8. The compound of claim 1 wherein the compound is selected from the group consisting of:

(+)-N-[5,6-dichloro-3-(4-chlorophenyl)-2-oxo-2,3-dihydro-1H-indol-3-yl]-2-(4-methylpiperazin-1-yl)acetamide (+)-N-[4,6-dichloro-3-(4-trifluoromethylphenyl)-2-oxo-2,3-dihydro-1H-indol-3-yl]-2-(1-ethylpiperid-4-yl)acetamide N-[4,6-dichloro-3-(4-chlorophenyl)-2-oxo-2,3-dihydro-1H-indol-3-yl]-2-(4-methylpiperazin-1-yl)acetamide N-[4-trifluoromethyl-6-cyano-3-(4-chlorophenyl)-2-oxo-2,3-dihydro-1H-indol-3-yl]-2-(4-ethylpiperazin-1-yl)acetamide (+)-N-[1-benzoyl-5,6-dichloro-3-(4-chlorophenyl)-2-oxo-2,3-dihydro-1H-indol-3-yl]-2-(4-methylpiperazin-1-yl)acetamide 3-(4-chlorophenyl)-3-[2-(4-ethylpiperazin-1-yl)acetylamino]-2-oxo-4-trifluoromethyl-2,3-dihydro-1H-indole-6-carboxamide N-[6-chloro-3-(4-chlorophenyl)-1,5-dimethyl-2-oxo-2,3-dihydro-1H-indol-3-yl]-2-(4-methylpiperazin-1-yl)acetamide (+)-N-[4,6-dichloro-3-(4-trifluoromethylphenyl)-2-oxo-2,3-dihydro-1H-indol-3-yl]-2-(1-ethyl-1,2,3,6-tetrahydropyrid-4-yl)acetamide N-[4,6-dichloro-3-(3,4-dichlorophenyl)-2-oxo-2,3-dihydro-1H-indol-3-yl]-2-(4-ethylpiperazin-1-yl)acetamide N-[4,6-dichloro-3-(3-fluoro-4-chlorophenyl)-2-oxo-2,3-dihydro-1H-indol-3-yl]-2-(4-ethylpiperazin-1-yl)acetamide N-[4,6-dichloro-3-(3-trifluoromethyl-4-chlorophenyl)-2-oxo-2,3-dihydro-1H-indol-3-yl]-2-(4-ethylpiperazin-1-yl)acetamide N-[4,6-dichloro-1-ethyl-3-(2-methylbenzo[b]thiophen-5-yl)-2-oxo-2,3-dihydro-1H-indol-3-yl]-2-(1-ethylpiperid-4-yl)acetamide N-[4,6-dichloro-1-ethyl-3-(2-methyl-5-benzofuryl)-2-oxo-2,3-dihydro-1H-indol-3-yl]-2-(4-ethylpiperazin-1-yl)acetamide N-[4,6-dichloro-3-(4-trifluoromethoxyphenyl)-2-oxo-2,3-dihydro-1H-indol-3-yl]-2-(4-ethylpiperazin-1-yl)acetamide in the form of the base or of an acid-addition salt.

9. A process for preparing a compound of formula (I)

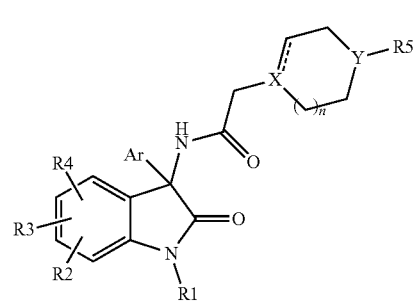

in which:

= represents a single or double bond,

X represents —N<, —CH< or

Y represents >N— or >CH—, wherein at least one from among X and Y represents N;

Ar represents an aryl or heteroaryl group optionally substituted with one or more substituents, which may be identical or different, chosen from halogen atoms and (C1-6)alkyl, (C1-6)haloalkyl, perhalo(C1-3)alkyl, (C1-6)alkoxy, perhalo(C1-3)alkoxy and aryl groups;

R1 represents a hydrogen atom or a (C1-6)alkyl, —C(=O)(C1-6)alkyl or —C(=O)aryl group;

R2, R3 and R4, which may be identical or different, located on any of the available positions of the phenyl nucleus, independently represent a hydrogen atom, a halogen atom, CN, OH, a (C1-6)alkyl group optionally substituted with a halogen atom or an OH; perhalo(C1-3)alkyl, (C1-6)alkoxy, perhalo(C1-3)alkoxy, aminocarbonyl, (C1-6)alkylaminocarbonyl, di(C1-6)alkylaminocarbonyl, aryl, aryloxy; heteroaryl; the aryl, aryloxy or heteroaryl group being optionally substituted with a halogen atom, CN, OH or a (C1-6)alkyl, perhalo(C1-3)alkyl or (C1-6)alkoxy group; whereby at least one from among R2, R3 and R4 is other than H;

R5 represents a (C1-6)alkyl or (C2-6)alkenyl group; and n represents 1 or 2;

in the form of the base or of an acid-addition salt; with the exclusion of 5-chloro-3-(2-chlorophenyl)-1,3-dihydro-3-[2-(4-methylpiperazin-1-yl)acetamido]indol-2-one; said process characterized in that it comprises a step that consists in reacting a compound of general formula (V):

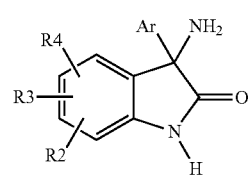

in which R2, R3, R4 and Ar are as defined according to formula (I) with a compound of formula (VI):

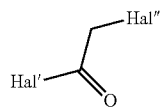  (VI)

in which Hal' and Hal", which may be identical or different, independently represent a halogen atom;

and then reacting the compound of formula (III) obtained

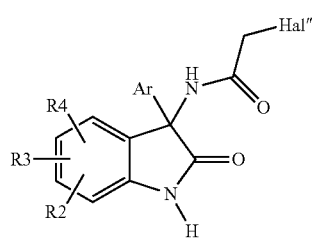  (III)

with a compound of general formula (IV):

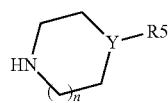  (IV)

in which R2, R3, R4, R5, Y, Ar and n are as defined in formula (I) and Hal" represents a halogen atom;

optionally followed by the step that consists in reacting the product of formula (I) obtained, in which X represents —N< and R1 is equal to H, with a compound of formula (II):

R1-Hal    (II)

in which R1, which is other than H, is defined as in formula (I) and Hal represents a halogen atom.

10. The process according to claim 9, further comprising a subsequent step that consists in separating out the compound of formula (I) and isolating same.

11. A process for preparing a compound of Formula I

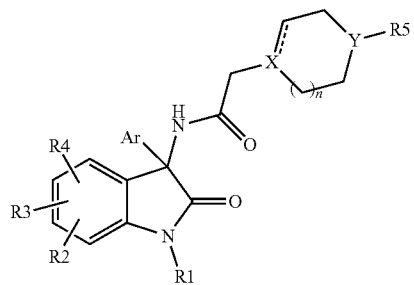  (I)

in which:
= represents a single or double bond,
X represents —N<, —CH< or

 ;

Y represents >N— or >CH—, wherein at least one from among X and Y represents N;

Ar represents an aryl or heteroaryl group optionally substituted with one or more substituents, which may be identical or different, chosen from halogen atoms and (C1-6)alkyl, (C1-6)haloalkyl, perhalo(C1-3)alkyl, (C1-6)alkoxy, perhalo(C1-3)alkoxy and aryl groups;

R1 represents a hydrogen atom or a (C1-6)alkyl, —C(=O)(C1-6)alkyl or —C(=O)aryl group;

R2, R3 and R4, which may be identical or different, located on any of the available positions of the phenyl nucleus, independently represent a hydrogen atom, a halogen atom, CN, OH, a (C1-6)alkyl group optionally substituted with a halogen atom or an OH; perhalo(C1-3)alkyl, (C1-6)alkoxy, perhalo(C1-3)alkoxy, aminocarbonyl, (C1-6)alkylaminocarbonyl, di(C1-6)alkylaminocarbonyl, aryl, aryloxy; heteroaryl; the aryl, aryloxy or heteroaryl group being optionally substituted with a halogen atom, CN, OH or a (C1-6)alkyl, perhalo(C1-3)alkyl or (C1-6)alkoxy group; whereby at least one from among R2, R3 and R4 is other than H;

R5 represents a (C1-6)alkyl or (C2-6)alkenyl group; and
n represents 1 or 2;

in the form of the base or of an acid-addition salt; with the exclusion of 5-chloro-3-(2-chlorophenyl)-1,3-dihydro-3-[2-(4-methylpiperazin-1-yl)acetamido]indol-2-one;

the process comprising the step of reacting a compound of formula (V)

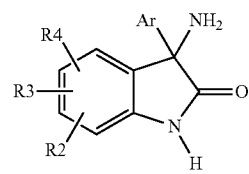  (V)

with a compound of formula (VIII):

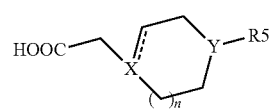  (VIII)

to form a compound of formula (I) in which R1 is hydrogen, and then optionally reacting the product of formula (I) obtained, in which R1 is equal to H, with a compound of formula (II):

R1-Hal    (II)

in which R1 in formula (II) is defined as in formula (I) with the proviso that R1 in formula (II) cannot be H, and Hal represents a halogen atom.

12. A process for preparing a compound of formula (I)

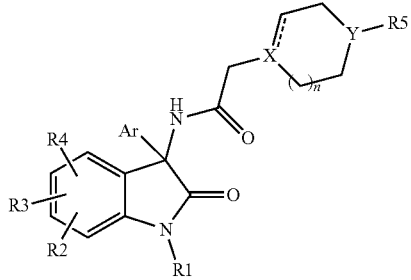

in which:
═ represents a single or double bond,
X represents —N<, —CH< or

Y represents >N— or >CH—, wherein at least one from among X and Y represents N;
Ar represents an aryl or heteroaryl group optionally substituted with one or more substituents, which may be identical or different, chosen from halogen atoms and (C1-6)alkyl, (C1-6)haloalkyl, perhalo(C1-3)alkyl, (C1-6)alkoxy, perhalo(C1-3)alkoxy and aryl groups;
R1 represents a hydrogen atom or a (C1-6)alkyl, —C(═O)(C1-6)alkyl or —C(═O)aryl group, R2, R3 and R4, which may be identical or different, located on any of the available positions of the phenyl nucleus, independently represent a hydrogen atom, a halogen atom, CN, OH, a (C1-6)alkyl group optionally substituted with a halogen atom or an OH; perhalo(C1-3)alkyl, (C1-6)alkoxhy, perhalo(C1-3)alkoxy, aminocarbonyl, (C1-6)alkylaminocarbon, di(C1-6)alkylaminocarbonyl, aryl, aryloxy; heteroaryl; the aryl, aryloxy or heteroaryl group being optionally substituted with a halogen atom, CN, OH or a (C1-6)alkyl, perhalo(C1-3)alkyl or (C1-6)alkoxy group; whereby at least one from among R2, R3 and R4 is other than H;
R5 represents a (C1-6)alkyl or (C2-6)alkenyl group; and
n represents 1 or 2;
in the form of the base or of an acid-addition salt; with the exclusion of 5-chloro-3-(2-chlorophenyl)-1,3-dihydro-3-[2-(4-methylpiperazin-1-yl)acetamido]indol-2-one; said process comprising the step of reacting a compound of formula (XXVIII):

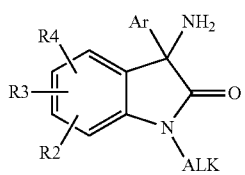

in which R2, R3, R4 and Ar are as defined according to formula (I) and ALK represents an alkyl group with a compound of formula (VI):

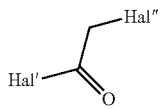

in which Hal' and Hal'', which may be identical or different, independently represent a halogen atom;
and then reacting the compound of formula (XXIX) obtained

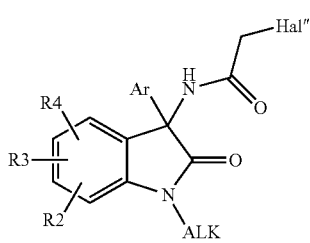

with a compound of formula (IV):

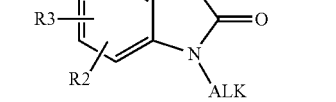

in which R2, R3, R4, R5, Y, Ar and n are as defined in formula (I), and Hal'' represents a halogen atom.

13. A process for preparing a compound of formula (I),

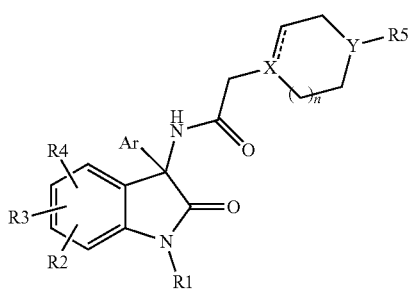

in which:
═ represents a single or double bond,
X represents —N<, —CH< or

Y represents >N— or >CH—, wherein at least one from among X and Y represents N;
Ar represents an aryl or heteroaryl group optionally substituted with one or more substituents, which may be identical or different, chosen from halogen atoms and (C1-6)alkyl, (C1-6)haloalkyl, perhalo(C1-3)alkyl, (C1-6)alkoxy, perhalo(C1-3)alkoxy and aryl groups;

R1 represents a hydrogen atom or a (C1-6)alkyl, —C(=O)(C1-6)alkyl or —C(=O)aryl group;

R2, R3 and R4, which may be identical or different, located on any of the available positions of the phenyl nucleus, independently represent a hydrogen atom, a halogen atom, CN, OH, a (C1-6)alkyl group optionally substituted with a halogen atom or an OH; perhalo(C1-3)alkyl, (C1-6)alkoxy, perhalo(C1-3)alkoxy, aminocarbonyl, (C1-6)alkylaminocarbonyl, di(C1-6)alkylaminocarbonyl, aryl, aryloxy; heteroaryl; the aryl, aryloxy or heteroaryl group being optionally substituted with a halogen atom, CN, OH or a (C1-6)alkyl, perhalo(C1-3)alkyl or (C1-6)alkoxy group; whereby at least one from among R2, R3 and R4 is other than H;

R5 represents a (C1-6)alkyl or (C2-6)alkenyl group; and n represents 1 or 2;

in the form of the base or of an acid-addition salt; with the exclusion of 5-chloro-3-(2-chlorophenyl)-1,3-dihydro-3-[2-(4-methylpiperazin-1-yl)acetamido]indol-2-one; said process comprising the step of reacting a compound of formula (XXVIII):

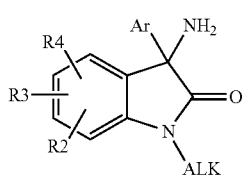

(XXVIII)

in which R2, R3, R4 and Ar are as defined according to formula (I) and ALK represents an alkyl group with a compound of formula (VII):

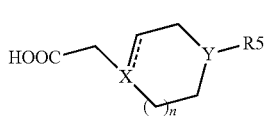

(VII)

in which ═, X, Y, R5 and n are as defined in formula (I).

14. A compound of formula (III):

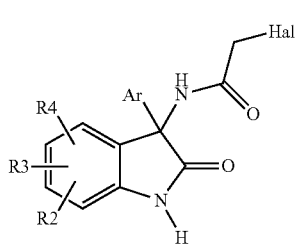

(III)

wherein R2, R3 and R4, which may be identical or different, located on any of the available positions of the phenyl nucleus, independently represent a hydrogen atom, CN, OH, a (C1-6)alkyl group optionally substituted with a halogen atom or an OH; perhalo(C1-3)alkyl, (C1-6)alkoxy, perhalo(C1-3)alkoxy, aminocarbonyl, (C1-6)alkylaminocarbonyl, di(C1-6)alkylaminocarbonyl, aryl, aryloxy; heteroaryl; the aryl, aryloxy or heteroaryl group being optionally substituted with a halogen atom, CN, OH or a (C1-6)alkyl, perhalo(C1-3)alkyl or (C1-6)alkoxy group; whereby at least one from among R2, R3 and R4 is other than H;

Ar represents a heteroaryl group optionally substituted with one or more substituents, which may be identical or different, chosen from halogen (C1-6)alkoxy, aryl, perhalo(C1-3)alkyl and (C1-6)alkyl groups with the proviso that the compound of formula (III) cannot be 5-chloro-3-(2-chloroacetamido)-3-(2-chlorophenyl)-1,3-dihydroindol-2-one.

15. A compound of formula (XXVIII):

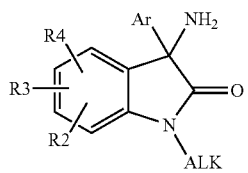

(XXVIII)

in which Ar represents an aryl or heteroaryl group optionally substituted with one or more substituents, which may be identical or different, chosen from halogen atoms and (C1-6)alkyl, (C1-6)haloalkyl, perhalo(C1-3)alkyl, (C1-6)alkoxy, perhalo(C1-3)alkoxy and aryl groups;

R2, R3 and R4, which may be identical or different, located on any of the available positions of the phenyl nucleus, independently represents a hydrogen atom, a halogen atom CN OH a (C1-6)alkyl group optionally substituted with a halogen atom or an OH; perhalo(C1-3)alkyl or (C1-6)alkoxy, perhalo(C1-3)alkoxy, aminocarbonyl, (C1-6)alkylaminocarbonyl, di(C1-6)alkylaminocarbonyl, aryl, aryloxy; heteroaryl; the aryl, aryloxy or heteroaryl group being optionally substituted with a halogen atom, CN, OH or a (C1-6)alkyl, perhalo(C1-3)alkyl or (C1-6)alkoxy group; wherein at least one from among R2, R3 and R4 is other than H; and ALK represents an alkyl group.

16. A compound of formula (XXIX):

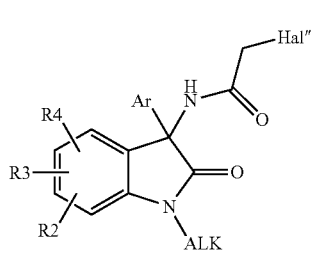

(XXIX)

in which Ar represents an aryl or heteroaryl group optionally substituted with one or more substituents, which may be identical or different, chosen from halogen atoms and (C1-6)alkyl, (C1-6)haloalkyl, perhalo(C1-3)alkyl, (C1-6)alkoxy, perhalo(C1-3)alkoxy and aryl groups;

R2, R3 and R4, which may be identical or different, located on any of the available positions of the phenyl nucleus independently reprsents a hydrogen atom, a halogen atom, CN, OH, a (C1-6)alkyl group optionally substituted with a halogen atom or an OH; perhalo(C1-3)alkyl, (C1-6)alkoxy, perhalo(C1-3)alkoxy, aminocarbonyl, (C1-6)alkylaminocarbonyl, di(C1-6)alkylaminocarbonyl, aryl, aryloxy; heteroaryl; the aryl, aryloxy or heteroaryl group being optionally substituted with a halogen atom, CN, OH or a (C1-6)alkyl, perhalo(C1-3)alkyl or (C1-6)alkoxy group; wherein at least one from among R2, R3 and R4 is other than H; ALK represents an alkyl group and Hal" represents a halogen atom.

17. A pharmaceutical composition comprising a compound of formula (I) of claim 1 and a pharmaceutically acceptable salt.

18. A combination comprising one or more compounds of claim 1 with one or more active ingredient(s) selected from anti-obesity and antidiabetic agents.

19. A combination comprising one or more compounds of claim 1 with a compound selected from rimonabant and metformin.

* * * * *